(12) United States Patent
Blazewicz et al.

(10) Patent No.: US 7,833,480 B2
(45) Date of Patent: *Nov. 16, 2010

(54) OXYGEN MONITORING APPARATUS AND METHODS OF USING THE APPARATUS

(75) Inventors: Perry R. Blazewicz, Tacoma, WA (US); Leslie E. Mace, Mercer Island, WA (US); Jerry R. Apperson, Lake Forest Park, WA (US)

(73) Assignee: RIC Investments, Inc., Wilmington, DE (US)

( * ) Notice: Subject to any disclaimer, the term of this patent is extended or adjusted under 35 U.S.C. 154(b) by 597 days.

This patent is subject to a terminal disclaimer.

(21) Appl. No.: 10/402,596

(22) Filed: Mar. 28, 2003

(65) Prior Publication Data

US 2003/0190262 A1    Oct. 9, 2003

Related U.S. Application Data

(63) Continuation of application No. 09/769,015, filed on Jan. 24, 2001, now Pat. No. 6,632,402.

(51) Int. Cl.
    *G01N 21/64* (2006.01)
(52) U.S. Cl. .................. 422/82.07; 422/82.08; 422/84; 422/91; 436/136; 436/138; 436/165; 436/172; 600/529; 600/532; 250/458.1; 250/459.1
(58) Field of Classification Search .............. 422/82.07, 422/82.08, 84, 91; 436/136, 138, 165, 172; 600/529, 532; 250/458.1, 459.1
See application file for complete search history.

(56) References Cited

U.S. PATENT DOCUMENTS 3,725,658 A * 4/1973 Stanley et al. ............... 250/364

(Continued)

FOREIGN PATENT DOCUMENTS

EP    0083703    7/1983

(Continued)

OTHER PUBLICATIONS

Journal of Clinical Monitoring and Computing, vol. 15, pp. 235-260 (1999).*

(Continued)

*Primary Examiner*—Jan M Ludlow

(57) ABSTRACT

Apparatus or systems which employ luminescence-quenching to produce a signal indicative of oxygen concentration. Components of such systems include: (1) an airway adapter, sampling cell, or the like having a casing and a sensor which is excited into luminescence with the luminescence decaying in a manner reflecting the concentration of oxygen in gases flowing through the airway adapter or other flow device and is in intimate contact with a window in the casing; (2) a transducer which has a light source for exciting a luminescable composition in the sensor into luminescence, a light sensitive detector for converting energy emitted from the luminescing composition as that the composition is quenched into an electrical signal indicative of oxygen concentration in the gases being monitored, and a casing which locates the light source and detector in close physical proximity to the window but on the side thereof opposite the sensor; and (3) subsystems for maintaining the sensor temperature constant and the temperature of the window above condensation temperature and for processing the signal generated by the light sensitive detector. Airway adapters, sampling cells, and transducers for such systems are also disclosed.

33 Claims, 13 Drawing Sheets

U.S. PATENT DOCUMENTS

| | | | |
|---|---|---|---|
| 4,632,807 A * | 12/1986 | Marsoner | 422/82.08 |
| 4,775,514 A | 10/1988 | Barnikol et al. | |
| 4,784,486 A | 11/1988 | VanWagenen et al. | |
| 4,914,720 A * | 4/1990 | Knodle et al. | 250/343 |
| 4,968,632 A | 11/1990 | Brauer et al. | |
| 5,030,420 A * | 7/1991 | Bacon et al. | 422/82.07 |
| 5,047,350 A | 9/1991 | Switalski et al. | |
| 5,092,342 A | 3/1992 | Hattendorff et al. | |
| 5,347,843 A | 9/1994 | Orr et al. | |
| 5,379,650 A | 1/1995 | Kofoed et al. | |
| 5,445,160 A * | 8/1995 | Culver et al. | 600/532 |
| 5,570,697 A | 11/1996 | Walker et al. | |
| 5,625,189 A | 4/1997 | McCaul et al. | |
| 5,863,460 A * | 1/1999 | Slovacek et al. | 252/301.35 |
| 6,325,978 B1 | 12/2001 | Labuda et al. | |
| 6,402,698 B1 | 6/2002 | Mault | |
| 6,468,222 B1 * | 10/2002 | Mault et al. | 600/531 |
| 6,815,211 B1 | 11/2004 | Blazewicz et al. | |

FOREIGN PATENT DOCUMENTS

| | | |
|---|---|---|
| WO | WO 00 42418 A | 7/2000 |

OTHER PUBLICATIONS

Kolle, C., et al., "Report, Optical Oxygen Sensor for Breath-Gas Analysis," Institute for Chemical and Optical Sensors, Report No. COS 95.001, Feb. 1995, 19 pages.

Office Action mailed Apr. 11, 2008, for Japanese counterpart Application No. 2002-559652, with English translation (2 pages).

* cited by examiner

OXYGEN MONITORING APPARATUS AND METHODS OF USING THE APPARATUS

CROSS-REFERENCE TO RELATED APPLICATION

This application is a continuation of application Ser. No. 09/769,015, filed Jan. 24, 2001 now U.S. Pat. No. 6,632,402.

BACKGROUND OF THE INVENTION

1. Field of the Invention

The present invention relates to the monitoring of oxygen concentration and, more particularly, to novel, improved methods and apparatus for monitoring the concentration of oxygen in respiratory and other gases.

2. State of the Art

The most common cause of anesthetic and ventilator related mortality and morbidity is inadequate delivery of oxygen to a patient's tissues. Therefore, the monitoring of static inspired oxygen concentration has long been a safety standard of practice to ensure detection of hypoxic gas delivery to patients undergoing surgery and to those on mechanical ventilators and receiving supplemental oxygen therapy. However, monitoring the static inspired fraction of inhaled oxygen does not always guarantee adequate oxygen delivery to the tissues because it is the alveolar oxygen concentration that eventually enriches the blood delivered to the cells.

It is this alveolar gas phase that is interfaced with pulmonary perfusion which, in turn, is principally responsible for controlling arterial blood gas levels. It is very important that the clinician know the blood gas levels (partial pressure) of oxygen ($pO_2$) and carbon dioxide ($pCO_2$) as well as the blood pH. Blood gas levels are used as an indication of incipient respiratory failure and in optimizing the settings on ventilators. In addition, blood gas levels can detect life-threatening changes in an anesthetized patient undergoing surgery:

The traditional method for obtaining arterial blood gas values is highly invasive. A sample of arterial blood is carefully extracted and the partial pressure of the gases is measured using a blood gas analyzer. Unfortunately, arterial puncture has significant limitations:

(1) arterial puncture requires a skilled health care provider and it carries a significant degree of patient discomfort and risk, (2) handling the blood is a potential health hazard to the health care provider, (3) significant delays are often encountered before results are obtained, and (4) measurements can only be made intermittently.

Noninvasive methods for estimating blood gas levels are available. Such methods include the use of capnography ($CO_2$ analysis). These methods employ fast gas analyzers at the patient's airway and give a graphic portrayal of breath-by-breath gas concentrations and, therefore, can measure the peak exhaled (end tidal) concentrations of the respective respired gases. Although gradients can occur between the actual arterial blood gas levels and the end tidal values, this type of monitoring is often used as a first order approximation of the arterial blood gas values.

Other techniques have been utilized for assessing patient blood gas levels with mixed results. Transcutaneous sensors measure tissue $pO_2$ and $pCO_2$ diffused through the heated skin surface. This type of sensor has a number of practical limitations including a slow speed of response and difficulty of use.

Pulse oximetry is widely used to measure the percentage of hemoglobin that is saturated with oxygen. Unfortunately, it does not measure the amount of dissolved oxygen present nor the amount of oxygen carried by the blood when the hemoglobin levels are reduced. This is important because low hemoglobin levels are found when there is a significant blood loss or when there is insufficient red blood cell information. In addition, pulse oximeter readings are specific to the point of contact, which is typically the finger or ear lobe, and may not reflect the oxygen level of vital organs during conditions such as shock or hypothermia.

Oxygraphy measures the approximate concentration of oxygen in the vital organs on a breath-by-breath basis and can quickly detect imminent hypoxemia due to decreasing alveolar oxygen concentration. For example, during hypoventilation, end tidal oxygen concentration changes more rapidly than does end tidal carbon dioxide. During the same conditions, pulse oximetry takes considerably longer to respond. Fast oxygen analysis (oxygraphy) can also readily detect inadvertent administration of hypoxic gas mixtures.

Oxygraphy reflects the balance of alveolar $O_2$ available during inspiration minus the $O_2$ uptake secondary to pulmonary perfusion. An increasing difference between inspiratory and end tidal oxygen values is a rapid indicator of a supply/demand imbalance which could be a result of changes in ventilation, diffusion, perfusion and/or metabolism of the patient. This imbalance must be quickly corrected because failure to meet oxygen demand is the most common cause of organ failure, cardiac arrest, and brain damage. Oxygraphy provides the earliest warning of the development of an impending hypoxic episode.

Oxygraphy has also been shown to be effective in diagnosing hypovolemic or septic shock, air embolism, hyperthermia, excessive positive-end expiratory pressure (PEEP), cardiopulmonary resuscitation (CPR) efficacy, and even cardiac arrest. During anesthesia, oxygraphy is useful in providing a routine monitor of preoxygenation (denitrogenation). It especially contributes to patient safety by detecting human errors, equipment failures, disconnections, misconnections, anesthesia overdoses, and esophageal intubations.

Combining the breath-by-breath analysis of oxygen with the measurement of airway flow/volume as outlined in U.S. Pat. Nos. 5,347,843 and 5,379,650 gives another dimension to the clinical utility of oxygraphy. This combination parameter, known as oxygen consumption ($VO_2$), provides an excellent overall patient status indicator. Adequate cardiac output, oxygen delivery, and metabolic activity are all confirmed by oxygen consumption because all of these physiological processes are required for oxygen consumption to take place. Oxygen consumption is also useful in predicting ventilator weaning success.

A metabolic measurement (calorimetry) includes determination of a patient's energy requirements (in calories per day) and respiratory quotient (RQ). Interest in the measurement of caloric requirements has closely paralleled the development of nutritional support. For example, the ability to intravenously provide all the necessary nutrition to critically ill patients has only been accomplished within the last 25 years. Along with the realization that we need to feed patients has come the need to know how much to feed them, what kind of nutrients (carbohydrates, lipids, protein) to feed them, and in what ratio the nutrients need to be supplied. The only true way to measure the caloric requirements of patients and to provide a noninvasive quality assessment of their response to nutrition is with indirect calorimetry. Airway $O_2$ consumption and $CO_2$ production can be measured noninvasively and provide a basis for the computations needed for a measurement of indirect calorimetry, a direct measurement of the metabolic status of the patient, and the patients' respiratory quotients.

With the above clinical need in mind, it is important to ensure that clinicians have the proper equipment to monitor breath-by-breath oxygen. While there are adequate devices for measuring static levels of oxygen, the measurement of breath-by-breath (fast) airway oxygen concentration requires more sophisticated instruments. Very few of these devices can be directly attached to the patient airway. Instead, most require the use of sampling lines to acquire the gas and send it to a remote site for analysis. Fast airway oxygen monitors are typically large, heavy, fragile instruments that consume considerable power. They must sample airway gases via a small bore plastic tube (sidestream) and remotely detect the oxygen gas as it passes from the airway to the sensor. The problems associated with this type of gas sampling are well known. Gas physics dictates painstaking, careful measurements because water vapor concentration pressure and temperature can vary within the patient's airway and gas sample line. The presence of water and mucous create problems for long term patency of the sample tube. Also, the sample line acts like a low pass filter and affects the fidelity of the measurement. Finally, the pressure variable delay introduced by the sample line creates difficulty in accurately synchronizing the airway flow and oxygen concentration signals required to calculate oxygen consumption.

On-airway (mainstream) monitoring of oxygen has the potential to solve all of the above problems, especially when breath-by-breath oxygen consumption measurements are made. However, most of the available fast oxygen sensors are simply too big, too heavy, too fragile, and/or otherwise not suited to be placed in line with a patient's breathing tube.

There are various other technologies which have been employed in monitoring airway oxygen concentration. Some of the most widely used are electrochemical sensors. These fall into two basic categories: polarographic cells and galvanic cells. These cells produce an electric current proportional to the number of oxygen molecules which diffuse across a membrane. The advantages of these types of sensors are simplicity and low cost. The disadvantages of these types of sensors include limited lifetime (chemistry depletes) and slow response (not breath-by-breath). In some cases, these cells have demonstrated sensitivity to certain anesthetic agents, which introduces inaccuracies into the oxygen concentration measurement. Generally, this type of sensor is too large to attach to the patient airway.

There have been a few reported developments where electrochemical cell membranes were improved to enable faster response. There are also silicon micromachined cells using the principle of "Back Cell" electrochemical technology. Their time response approaches 150 ms but they appear to be subject to the typical problems of this type of cell (i.e., stability and calibration).

Another popular medical oxygen sensor is the paramagnetic type. This sensor uses the strong magnetic property of oxygen as a sensing mechanism. There are two basic types of paramagnetic cells: static and dynamic. The static type is a dumbbell assembly suspended between the poles of a permanent magnet. The magnetic forces of the surrounding oxygen molecules cause a torsional rotation of the dumbbell which can be sensed optically and employed as a measure of oxygen concentration. The dynamic type (see U.S. Pat. No. 4,633,705) uses a magneto-acoustic approach. This requires a gas sample and a reference gas that are mixed within an electromagnetic field. When the field is switched on and off, a pressure signal proportional to the oxygen content is generated. The signal can be detected by a differential microphone. The advantages of the paramagnetic sensor are good linearity and stability. The dynamic type has an inherently faster response than the static type. Both types are subject to mechanical vibration, and the dynamic type has the disadvantage of requiring a reference gas. Neither type is suitable for on-airway applications.

Zirconium oxide cells are frequently used in the automotive industry to measure oxygen concentration. The cell is constructed from a solid electrolyte tube covered by platinum electrodes. When heated to approximately 800 degrees C., a voltage proportional to the logarithm of the ratio between a sample gas and a reference gas is generated. The advantages of this sensor are wide dynamic range, very fast response, and simplicity. The high cell temperature is clearly a disadvantage as is power consumption. Also, the cell is degraded in the presence of anesthetic agents. Clearly, this type of cell cannot be used on a patient airway.

Ultraviolet absorption uses the principle that oxygen exhibits absorption properties in the ultraviolet part of the electromagnetic spectrum (about 147 nm). This technique has been used in several medical applications but has never been reduced to commercial viability. There are numerous technical difficulties which make this a difficult technique for on-airway applications.

Mass spectrometers spread ionized gas molecules into a detectable spectrum according to their mass-to-charge ratios and can accordingly be used to measure oxygen concentration. These instruments are generally large assemblies with ionizing magnets and high vacuum pumps. The advantages of mass spectrometers include high accuracy, multi-gas analysis capability, and rapid response. The disadvantages include high cost, high power consumption, and large size. Mass spectrometers are not suitable for on-airway applications.

Raman scattering spectrometers (as described in U.S. Pat. No. 4,784,486) can also be used to measure oxygen concentration. These devices respond to photons emitted by the collision of a photon with an oxygen molecule. A photon from a high-power laser loses energy to the oxygen molecule and is re-emitted at a lower energy and frequency. The number of photons re-emitted at the oxygen scattering wavelength is proportional to the number of oxygen molecules present. Like mass spectrometers, Raman spectrometers have multi-gas analysis capability and rapid response time. Disadvantages include large size and power consumption. Therefore, Raman scattering photometers are not suitable for on-airway applications.

Visible light absorption spectrometers (as described in U.S. Pat. Nos. 5,625,189 and 5,570,697) utilize semiconductor lasers that emit light at near 760 nm, an area of the spectrum comprised of weak absorption lines for oxygen. With sophisticated circuitry, the laser can be thermally and/or electronically tuned to the appropriate absorption bands. The amount of energy absorbed is proportional to the number of oxygen molecules present. The advantages of this system are precision, fast response, and no consumable or moving parts. The disadvantages include somewhat fragile optical components, sensitivity to ambient temperature shifts, and a long gas sample path length. While there have been attempts to utilize this technology in an on-airway configuration, no commercially viable instruments have so far been available.

Luminescence-quenching has also been proposed as a technique for measuring oxygen concentration. In this approach, a sensor contacted by the gases being monitored is excited into luminescence. This luminescence is quenched by the oxygen in the monitored gases. The rate of quenching is related to the partial pressure of oxygen in the monitored gases, and that parameter can accordingly be used to provide an indication of the oxygen in the monitored gases. However, the prior art does not disclose an oxygen concentration monitor employing luminescence-quenching which addresses the problems associated with this type of measurement device in any practical application. These problems include: photo-degradation-associated and other instabilities of the sensor, low signal level, noise leading to difficulties in assessing the decay of sensor luminescence, acceptably fast response times, thermal drift of the sensor, reproducibility of the sensors, inaccuracies attributable to stray light reaching the data photodetector, and the need for light weight, ruggedness, and low power consumption. Disclosed in copending applications Ser. Nos. 09/128,918 and 09/128,897, both filed Aug. 4, 1998, are devices for monitoring oxygen concentration in gaseous mixtures which differ from the majority of the oxygen monitors described above in that they are compact, lightweight, and otherwise suited for on-airway mainstream monitoring of the oxygen concentration in a person's respiratory gases. These monitoring devices utilize the fast (or breath-by-breath) approach to oxygen concentration monitoring with the quenching of a luminescent dye being used in determining the concentration of oxygen in the gases being monitored.

Fast (breath-by-breath) monitoring of end tidal oxygen is an important diagnostic tool because, as examples only:
1. It is a sensitive indicator of hypoventilation.
2. It aids in rapid diagnosis of anesthetic/ventilation mishaps such as (a) inappropriate gas concentration, (b) apnea, and (c) breathing apparatus disconnects.
3. End tidal oxygen analysis reflects arterial oxygen concentration.
4. Inspired-expired oxygen concentration differences reflect adequacy of alveolar ventilation. This is useful for patients undergoing ECMO (Extracorporeal Membrane Oxygenation) or nitric oxide therapies.
5. When combined with a volume flow device (e.g. a pneumotach), $VO_2$ (oxygen consumption) can be determined. Oxygen consumption is a very useful parameter in determining (a) oxygen uptake during ventilation or exercise, (b) respiratory exchange ratio or RQ (respiratory quotient) and (c) general patient metabolic status.

The novel sensor devices disclosed in the copending applications locate a luminescent chemical in the patient airway. Modulated visible light excites the chemical and causes it to luminesce. The lifetime of the luminescence is proportional to the amount of oxygen present. A transducer containing a photodetector and associated electronic circuitry measures decay time and relates the measured parameter to the ambient oxygen partial pressure.

The transducer device is small (<1 cubic inch), lightweight (less than 1 ounce), and does not contain moving parts. It utilizes visible light optoelectronics and consumes minimal power (system power less than 2 watts). The unit warms up in less than 30 seconds, which is advantageous in on-airway applications because of the need to take prompt remedial action if a change occurs in a patient's condition reflected in a change in respiratory oxygen concentration. The assembly does not require any significant optical alignment and is very rugged (capable of being dropped from 6 feet without affecting optical alignment or otherwise damaging the device).

The principles of the inventions disclosed in the copending applications can be employed to advantage in sidestream (sampling) type systems as well as in mainstream systems. This is important because some gas analysis systems, such as anesthetic analyzers, employ sidestream techniques to acquire their gas sample.

A typical transducer unit is easy to calibrate, is stable (±2 torr over 8 hours at a 21 percent oxygen concentration), and has a high resolution (0.1 torr) and a wide measurement range (oxygen concentrations of 0 to 100 percent). Response to changing oxygen concentrations is fast (<100 ms for oxygen concentrations of 10-90 percent at flow rates ≈1 l/min). The transducer is not susceptible to interference from anesthetic agents, water vapor, nitrous oxide, carbon dioxide, or other gases and vapors apt to be present in the environment in which the system is used.

The sensor comprises a polymeric membrane in which a luminescable composition such as a porphyin dye is dispersed. The sensor membrane is the mediator that brings about dye-oxygen interaction in a controlled fashion. In a functional sensor, the dye is dispersed in the polymeric membrane, and oxygen diffuses through the polymer. The characteristics of the sensor are dependent upon the dye-polymer interaction and permeability and the solubility of oxygen in the polymer. Such characteristics include the sensitivity of response of the sensor to oxygen, the response time of the sensor to a change in oxygen concentration, and the measured values of phosphorescence intensity and decay time. Thus the composition and molecular weight of the polymer determines the sensor characteristics. Also, if the sensor is prepared by evaporation of a solution as described in the copending applications, the film characteristics depend on the solvent that is used and conditions during casting or evaporation. If the dye is separately doped into the film from another solution, the solvent and conditions in the doping medium also affect the sensor characteristics. When the polymer film is prepared by polymerization of a monomer or mixture, the sensor characteristics depend on the conditions of polymerization and such resultant polymer characteristics as degree of crosslinking and molecular weight.

The luminescent chemical sensor is not toxic to the patient and is a part of a consumable (i.e., disposable) airway adapter weighing less than 0.5 ounce. The sensor shelf life is greater than one year and the operational life exceeds 100 hours. The cost of the consumable airway adapter is minimal.

It is also important that the oxygen monitoring systems disclosed in the copending applications have sufficient accuracy (1.0%), precision (0.01%), and response time (<100 ms) to monitor breath-by-breath oxygen concentrations. The sensor is not sensitive to other gases found in the airway, including anesthetic agents, and is accordingly not excited into luminescence by those gases. The sensitivity of the sensor to temperature, flow rate, pressure and humidity change is well understood, and algorithms which provide compensation for any errors due to these changes are incorporated in the signal processing circuits of the device.

The visible light oxygen measurement transducers disclosed in the copending applications employ a sensor heater arrangement and a proportional-integrated-differential (PID) heater control system for keeping the oxygen concentration sensor of the transducer precisely at a selected operating temperature. This is particularly significant because those oxygen measurement transducers employ a sensor which involves the use of the diffusion of oxygen into a luminescable layer in measuring oxygen concentration. The rate of diffusion is temperature dependent. As a consequence, the measurement of oxygen concentration becomes inaccurate unless the sensor temperature is kept constant. Also, if the window through which the excitation energy passes is not kept warm, it may fog over. This also affects the accuracy of the oxygen concentration measurement.

The location of the oxygen concentration sensor in a replaceable, simple component is a feature of the systems disclosed in the copending applications. This makes it possible to readily and inexpensively ensure that the system is sterile with respect to each patient being monitored by replacing the airway adapter between patients, avoiding the non-desirability (and perhaps the inability) to sterilize that system component.

The provision of an airway adapter sensor and a separate signal-producing transducer also has the practical advantage that a measurement of oxygen concentration can be made without interrupting either the ventilation of a patient or any other procedure involving the use of the airway circuit. This is effected by installing the airway adapter in the airway circuit. When the time comes to make oxygen measurements, all that is required is that the transducer be coupled to the airway adapter already in place.

Another important feature of the invention ensures that the airway adapter and transducer are assembled in the correct orientation and that the airway adapter and transducer are securely assembled until deliberately separated by the system user.

The signals generated by the oxygen-measurement transducers of the previously disclosed system are processed to remove noise and extract the luminescence decay time, which is the oxygen-sensitive parameter of interest. A lock-in amplifier is preferably employed for this purpose. The lock-in amplifier outputs a signal which has a phase angle corresponding to the decay time of the excited, luminescent composition in the oxygen concentration sensor. The lock-in detection circuitry rejects noise and those components of the photodetector-generated signal which are not indicative of oxygen concentration. This noise reduction also allows a higher level of signal gain which, in turn, makes possible enhanced measurement precision while decreasing the level of the visible excitation. This reduces instability from photo-aging of the sensor, increasing accuracy and useable life. All of this processing, which can be done with digital, analog, or hybrid method, is fast enough for even the most demanding applications such as those requiring the breath-by-breath monitoring of a human patient. Various pathological conditions result in a change of oxygen demand by the body. If a decrease of oxygen utilization by the body, for example, can be detected on a breath-by-breath basis, timely and effective remedial steps can be taken to assist the patient.

In the novel oxygen measurement transducers of the present invention, the concentration of oxygen in the gases being monitored is reflected in the quenching of an excited luminescent composition in the oxygen concentration sensor by oxygen diffusing into the sensor matrix. A source consisting of a light-emitting diode (LED) produces visible exciting light which strikes the surface of the sensor film. Some of the light is absorbed by the luminescent chemical dye in the film whereupon it produces luminescent light at a second, shifted wavelength. This light is captured by a photodetector which thereupon generates a signal reflecting the intensity and decay pattern of the intercepted light. All light directed toward the photodetector can potentially result in a signal. A suitable optical filter placed over the surface of the photodetector discriminates against all but the luminescent light, thereby ensuring that the photodetector is producing a signal related to oxygen concentration only.

SUMMARY OF THE INVENTION

There have now been invented and disclosed herein new and novel oxygen concentration measuring devices which differ from those disclosed in the copending applications in that the light-sensitive, oxygen concentration sensor is located on the same side of the gas sampling device (typically an airway adapter or a sampling cell) as the light source and detector of an associated transducer.

This "single-sided" arrangement of the light source, oxygen sensor, and photodetector has a number of significant advantages. Specifically, in the systems disclosed in the copending applications, intimate contact between heater element components of the transducer and the sampling device is required, and this can prove difficult to achieve. This problem is eliminated in the single-sided systems disclosed herein by supporting the sensor from a near side optical window and by heating that window which thereupon transfers thermal energy to the associated sensor.

Another important advantage of the single-sided arrangements disclosed herein is that the energy of excitation indicative of oxygen concentration does not have to traverse the gases flowing through the sampling component. Consequently, the degradation in signal attributable to interactions between the gas being sampled and the energy of excitation is eliminated, making a significantly less-degraded signal available to the photodetector.

One of the two apertures present in the sampling component of the previously disclosed systems is eliminated, along with a sensor film heating component installed in that aperture. This leads directly to a less complex, less expensive sampling component. This is important because the sensor film has a finite, relatively short life, and the sampling unit must accordingly be periodically replaced. In fact, in an important application of the present invention—on-airway use in a hospital—it is highly desirable that the cost of the sampling unit be low enough to make it feasible to discard this unit after a single use.

The location of the sensor film on the opposite side of a flow passage from an optical window in the previously disclosed systems leaves the optical window essentially unheated, making it particularly prone to fogging. Contamination of this window may also be a problem, creating obstructions in the optical path between the sensor and the window.

The single-sided arrangement also makes feasible systems embodying the principles of the present invention where it is desirable to have a unit such as a freestanding film reader in close proximity to the sensor film as can be done with fiber-optics, for example. Such arrangements can be beneficially used in sensor film quality control and in transcutaneous oxygen monitoring, for example. Such arrangements are made practical by employing the principles of the present invention because the sensor film is associated with the optical window and not isolated from the exterior of the sampling component by a thermal component as disclosed in the copending applications.

Systems with the advantages just described differ physically from those disclosed in the copending applications in that the optical window in the airway adapter or sampling cell is employed as a mount or support for the sensor film and is also employed to transfer to the film the heat needed to keep it at a constant temperature. As will be apparent, this also results in the window being heated to a high enough temperature to eliminate fogging. Various schemes for heating the transparent window might be employed. One suitable approach is to surround the transparent window of the gas sampling device with a heater in a ring configuration. Of importance in systems employing the principles of the present invention is a secure application of the film-type sensor to the optical window of the sampling device. An adhesive layer may be employed to bond the sensor film to the window, or it may be solvent bonded to the window. Another approach is to employ a retaining ring to stretch the film over and secure it to the window. A related approach is to employ a retaining ring bounded on one side with a fine mesh to retain the film and press it against the window. The last-mentioned approach has the advantage that the film is physically retained without an adhesive and will not loosen. In addition, the mesh, with its location on the gas side of the sensor, enhances heat conduction over that side of the sensor, producing exceptional thermal stability.

In monitoring apparatus embodying the principles of the present invention, light not indicative of the concentration of oxygen in the gas being monitored is preferably kept from the detector of that apparatus by locating a blue dichroic filter and an infrared-blocking filter in line with and on the output side of the light source and by summarily locating a red dichroic filter and a red glass filter in front of the detector apparatus. Because this arrangement eliminates essentially all of the light which is not part of the signal indicative of oxygen concentration, the light collection efficiency is increased to the extent that the intensity of the exciting light from the LED or other source can be reduced. This is important because reducing the intensity of the light from the source significantly increases the service life of the sensor. This is particularly significant in sidestream applications of the present invention where the sensor is not apt to be replaced each time it is used.

Other objects, advantages, and features of the present invention will be apparent to the reader from the foregoing and the appended claims, and as the ensuing detailed description and discussion is read in conjunction with the accompanying drawings.

BRIEF DESCRIPTION OF THE OF THE DRAWINGS

In the drawings, like reference numerals refer to like parts throughout the various views.

DETAILED DESCRIPTION OF THE INVENTION

The descriptions contained herein adhere to a numbering convention intended to facilitate understanding and make for easy cross-referencing of described features between figures. In this convention, the first digit (for features indicated by a three-digit reference number) or the first two digits (for features indicated by a four-digit reference number) correspond(s) to the figure number in which the feature is first described. Like features are thus identified by the same reference number throughout the detailed description. In some instances, features described by the same reference number may have a different physical appearance in two or more figures. In this case, the use of a like reference number is especially useful in drawing the attention of the reader to various physical embodiments that a given feature of the invention may have. Features first introduced within the same figure are numbered more-or-less consecutively in a manner corresponding to the order in which they are described.

In each instance, physical forms depicted herein are intended to be illustrative of particular embodiments of the invention. They are given such particular physical form to facilitate understanding. In no case is the choice of a particular physical form intended to be limiting unless specifically so stated. A reader skilled in the art will readily recognize many alternative but equivalent physical embodiments, each of which is intended to fall within the scope of the invention taught herein.

Figure 1:
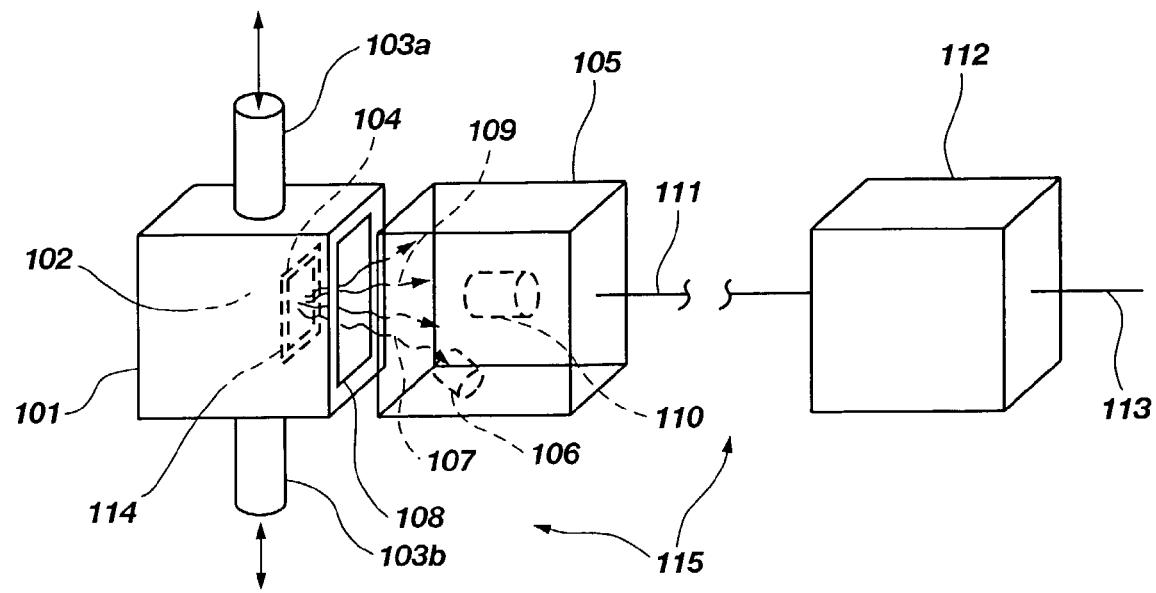
FIG. 1 is a block diagram of several main elements of a luminescence-quenching gas detection apparatus of the present invention showing general interrelationships between the main elements.

Referring now to the figures, and in particular to FIG. 1, there is illustrated a block diagram showing the main components and relationships therebetween of a luminescence-quenching oxygen concentration monitoring apparatus in accordance with the principles of the present invention. A cuvette or airway adapter 101 contains a volume 102 that serves as a gas sampling cell. For applications requiring sidestream sampling of respiration or other gases, inlet/outlet ports 103a and 103b provide means for introduction of the gas to the sampling volume 102 (also referred herein as "sensing volume 102") and venting of gas from the sampling volume, respectively. For mainstream applications and other applications requiring bidirectional transmission of the gas through the sampling volume 102, the role of inlet/outlet ports 103a and 103b alternates with respect to the instantaneous direction of gas passage therethrough. A sensing film 104 held in intimate contact with gas in the sampling cell provides a medium for a luminescence-quenching reaction that forms the basis of the measurement technique of the present invention.

A transducer 105 is closely coupled to the cuvette 101 so as to allow a light source 106 to illuminate the sensing film 104 with electromagnetic radiation. The light or excitation energy emitted from light source 106 is illustrated as a wavy line 107. For many applications, it is desirable for the sampling volume 102 to be isolated from the transducer 105. In these cases, an aperture 108 may take the form of a window set into the housing of airway adapter 101 or may be formed integrally therein.

According to the reaction used for gas measurement, light or excitation energy 107 causes the sensing film 104 to emit a luminescence, indicated by wavy lines 109, in a substantially omnidirectional manner at a wavelength different from that of the excitation energy 107. The emitted luminescence or luminescent energy 109 falls on a photodetector 110 for measurement. The intensity and persistence of this luminescence rises and falls according to the concentration of one or more gas components contained within the sampling volume 102. In a preferred embodiment of the present invention, oxygen causes a modification of the intensity and persistence of the luminescent energy by quenching the luminescence reaction as its concentration increases. Thus the luminescence-quenching reaction is used to measure the amount of oxygen available to reaction sites within the sensing film 104. The quantity of oxygen available to the reaction sites may, in turn, be related to its partial pressure or concentration within the measured gas.

According to a preferred embodiment of the present invention, light source 106, which may be in the form of a blue or green light-emitting diode (LED), is pulsed so as to provide to the sensing film 104 excitation energy 107 that varies in time. Accordingly, luminescent energy 109 emitted from the film varies in time at a substantially red wavelength. The photodetector 110, in turn, senses a cyclical variation in emitted energy, the persistence and intensity of which is proportional to the oxygen concentration of the gas introduced into the sampling volume 102 of the airway adapter 101. The inventors have discovered that for many applications, the persistence of the emitted luminescent energy 109 forms a more reliable and repeatable basis for measurement of oxygen concentration than does the intensity or amplitude of the emitted energy.

Transducer 105 is connected to control and measurement circuitry 112 by means of electrical connections indicated by the line 111. Control and measurement circuitry 112 may, in turn, be connected to an external computer, communication, display or other device by means of connections 113.

A temperature regulation apparatus 114, which, in a preferred embodiment, is a heater held in intimate contact with the sensing film 104, is maintained in a relationship to the sensing film to provide adequate control of film temperature while not interfering with the light transmission paths of excitation energy 107 and luminescence energy 109. As will be appreciated by the following discussion, control of sensing film temperature is important to the luminescence-quenching rate as a function of oxygen concentration.

Taken together, the components of the block diagram illustrated in FIG. 1 form an oxygen concentration monitoring apparatus 115.

Figure 2:
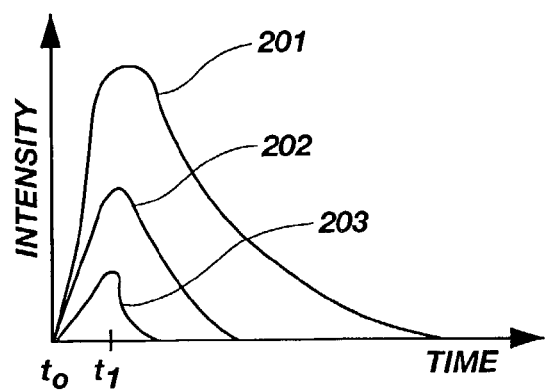
FIG. 2 is a graph that depicts characteristic emission curves of an excited sensing film of the present invention showing qualitative emission intensity vs. time.

Turning our attention now to FIG. 2, there is illustrated a qualitative graph showing the relationship of the intensity and persistence of luminescence in the sensing film as they may vary with oxygen concentration. The vertical axis is an arbitrary indication of intensity or brightness of the luminescence, while the horizontal axis is an arbitrary indication of time. While no units are given in the illustration, the total time scale of the horizontal axis is generally well under 1 second.

For purposes of understanding FIG. 2, one may assume that excitation energy begins to illuminate the sensing film at $t_0$ and ceases at $t_1$. Curve 201 indicates the natural luminescence of the sensing film in the absence of oxygen. Higher concentrations of oxygen progressively decrease both the peak luminescence and the luminescence decay time. Curve 202 illustrates the effect of luminescence-quenching in the presence of a moderate oxygen concentration of, for example, 21% at 1 atmosphere pressure. Curve 203 shows a higher degree of luminescence-quenching caused by a higher oxygen concentration of, for example, 50% at 1 atmosphere pressure.

By inspection of FIG. 2, one can see that both the peak luminance and the decay time decrease as oxygen concentration increases. By measuring the decay time over a series of excitation pulses, real-time measurement of oxygen concentration is effected.

It is of particular note that characteristic luminescence response of the sensing film 104 as a function of oxygen concentration is a strong function of film temperature. This is due to the fact that it is the presence of oxygen within the sensing film at the site of each luminescence reaction that determines whether or not that particular luminescence reaction will be quenched. In this manner, it is the statistical proximity of oxygen molecules to the population of luminescence reaction sites within the sensing film that determines the overall macroscopic luminescence-quenching effect illustrated by curves 201, 202, and 203. The presence and concentration of oxygen within the sensing film 104 is a function of the rate of diffusion of oxygen within the film. As with most or all diffusion rate-limited reactions, oxygen luminescence-quenching is thus a strong function of temperature. Accordingly, embodiments of temperature regulation apparatus play a significant role in the enablement of the present invention.

Figure 3:
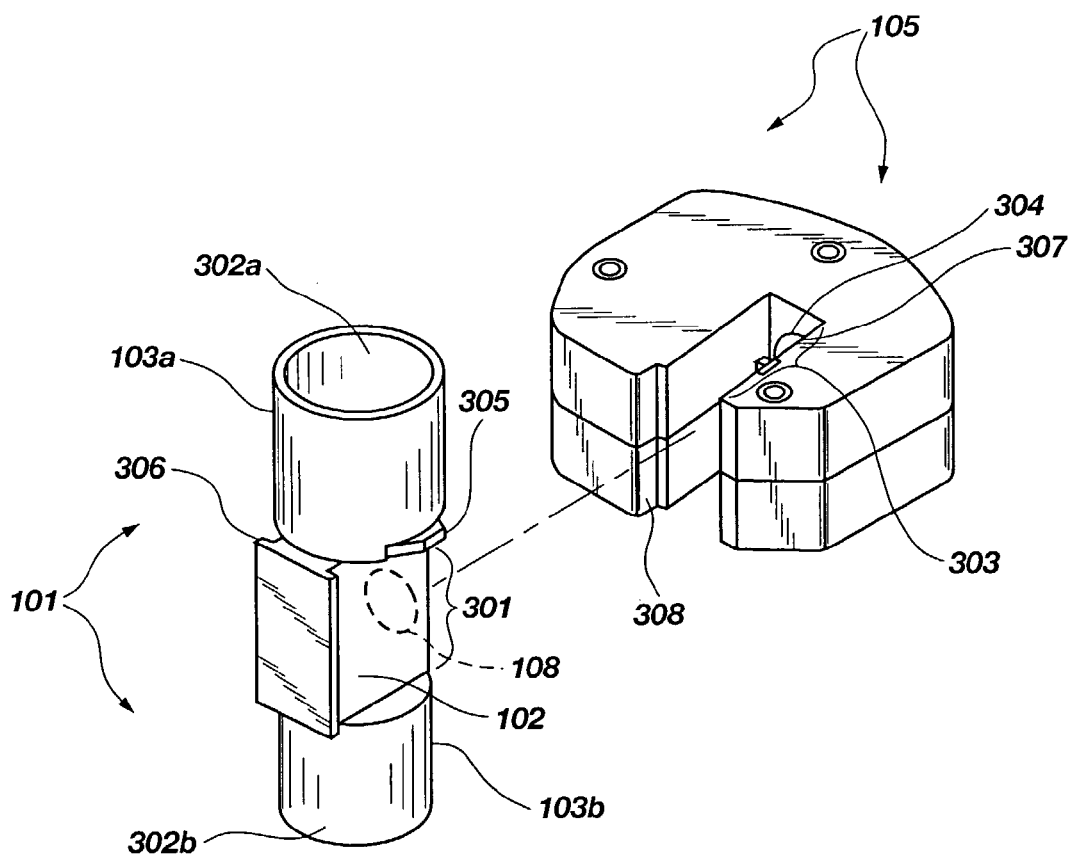
FIG. 3 is a perspective view of an airway adapter and a complementary transducer that shows a particular physical embodiment of a portion of the block diagram of FIG. 1.

Referring now to FIG. 3, there illustrated is a perspective view of an embodiment of certain parts of the present invention wherein the sampling cell is in the form of a mainstream airway adapter. The airway adapter 101 includes inlet/outlet ports 103a and 103b respectively. Aperture 108 is indicated by dashed lines and lies on an unseen side of the airway adapter. A transducer 105 is formed to securely attach to the airway adapter 101 by a snap fit, for instance. By forming the sampling cell and transducer in separate couplable bodies, the airway adapter 101 may readily be made replaceable or even disposable without incurring the extra cost of replacing all the optical and signal conditioning components every time an airway adapter is discarded. It is particularly advantageous to form the sampling cell as a disposable unit for mainstream applications so that each patient can be provided with his or her personal airway adapter without fear of contamination by another individual. Making the airway adapter replaceable also serves to make connection of oxygen monitoring apparatus quick and easy and allows the more expensive transducers to be easily shared among multiple patients without causing an interruption in airway flow while removing or inserting a measuring apparatus. Finally, making the mainstream airway adapter disposable also ensures that fresh sensing films are provided to each patient. This is important due to a tendency for the sensing film to gradually undergo photo-degradation.

The mainstream airway adapter body 101 may be comprised of any of a number of suitable materials. In one embodiment, airway adaptor 101 is a one-piece unit typically molded from Valox polycarbonate or a comparable polymer that is rugged and can be molded to close tolerances. An opaque material is employed to keep ambient light from reaching the sensing film 104 through the walls of the airway adapter. Such extraneous light would adversely affect the accuracy of the oxygen concentration reading that the system is designed to provide, or at least degrade the signal-to-noise ratio of the characteristic signal, thus requiring more sophisticated and expensive control and detection means.

Airway adapter 101 has a generally parallelepipedal center section 301 and hollow, cylindrical inlet/outlet ports 103a and 103b at opposite ends of center section 301. Axially aligned passages 302a, 102, and 302b found in airway adapter elements 103a, 301, and 103b, respectively, define a flow passage extending from end-to-end of airway adapter 101. Port section 103a may be configured as a female connector and port 103b may be configured as a male connector, thus allowing the airway adapter to be connected to conventional anesthetic and respiratory circuits.

The center section 301 of the airway adapter 101 is formed so as to fit snugly into a correspondingly shaped section 303 of transducer 105. When airway adapter 101 is properly snapped into transducer 105, aperture 108 in the airway adapter is held in an orientation relative to a corresponding aperture 304 so as to allow passage of light therebetween. As described and shown in FIG. 1, excitation energy 107 (see FIG. 1) comprised of blue or green light is transmitted from transducer 105, through apertures 304 and 108, and into contact with a sensing film 104 (see FIG. 1) held in intimate contact with the gas contained within sensing volume 102. In response, and with a signal strength and duration characteristic of the oxygen concentration of the gas in sensing volume 102, the sensing film 104 emits electromagnetic radiation back through apertures 108 and 304 onto a photodetector 110 (see FIG. 1) held inside transducer 105 with a field of view comprising at least a portion of the sensing film 104 (through apertures 304 and 108). In a preferred embodiment, apertures 108 and 304 contain windows which permit the transmission of both excitation and luminescence radiation therethrough.

Incorrect assembly of the airway adapter 101 into transducer 105 is precluded by the inclusion of location features such as stops 305 and 306 on the airway adapter 101 and complementary stops 307 and 308, respectively, on the transducer 105.

Figure 4:
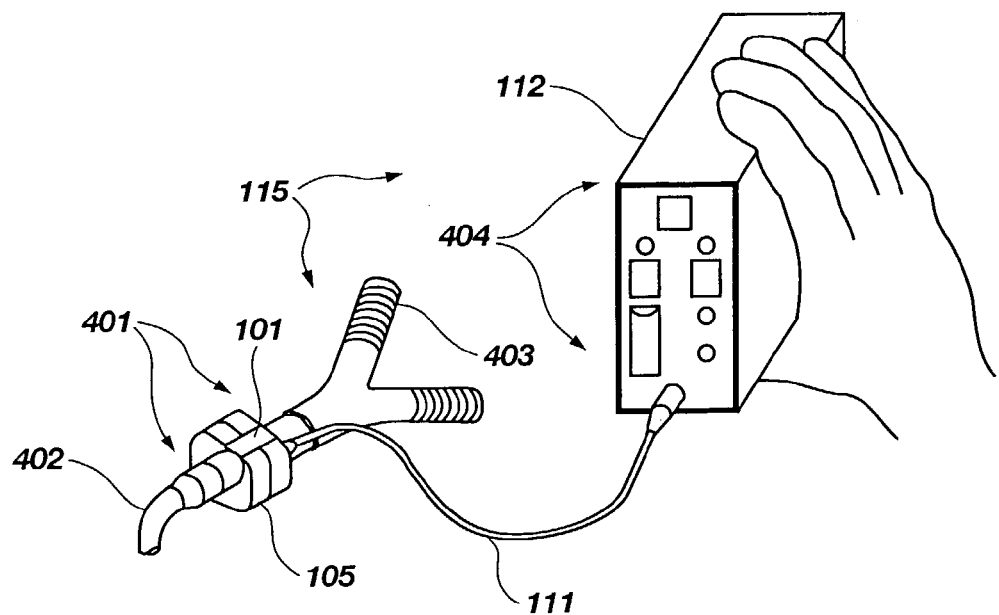
FIG. 4 is a generally pictorial view of an inline system for monitoring the oxygen concentration in a patient's breath.

FIG. 4 depicts an oxygen concentration monitoring apparatus or system 115 as it may be used in operation. A mainstream airway adapter 101 and transducer 105, as illustrated in FIG. 3, make up the major components of inline assembly or system 401. The monitoring system 115 illustrated in FIG. 4 also includes a hand-held control and measurement circuitry display unit 112 that is connected to transducer 105 by a conventional electrical connection 111.

In the particular application of the present invention illustrated in FIG. 4, system 115 is employed to monitor the concentration of oxygen in a patient's respiratory gases. To this end, airway adapter 101 is connected in line between an endotracheal tube 402 inserted in the patient's trachea and the breathing circuit 403 of a mechanical ventilator (not shown).

Airway adapter 101 and transducer 105 cooperate to produce an electrical signal indicative of the oxygen concentration in the gases flowing from endotracheal tube 402 through airway adapter 101 to breathing circuit 403. This signal is transmitted to unit 112 through electrical connection 111 and converted to a numerical designation that appears on the display array 404 of unit 112.

The two-component system 401 just described meets the requirement that monitoring be accomplished without interrupting the flow of gases through breathing circuit 403 or other patient-connected flow circuit. Transducer 105 can be removed—for example, to facilitate or enable the movement of a patient—leaving airway adapter 101 in place to continue the vital flow of gases.

System 115 has, in this regard, the advantage that there are no electrical components in the airway adapter. Hence, there are no potentially dangerous electrical connections to the airway adapter which might expose the patient to an electrical shock.

Figure 5:
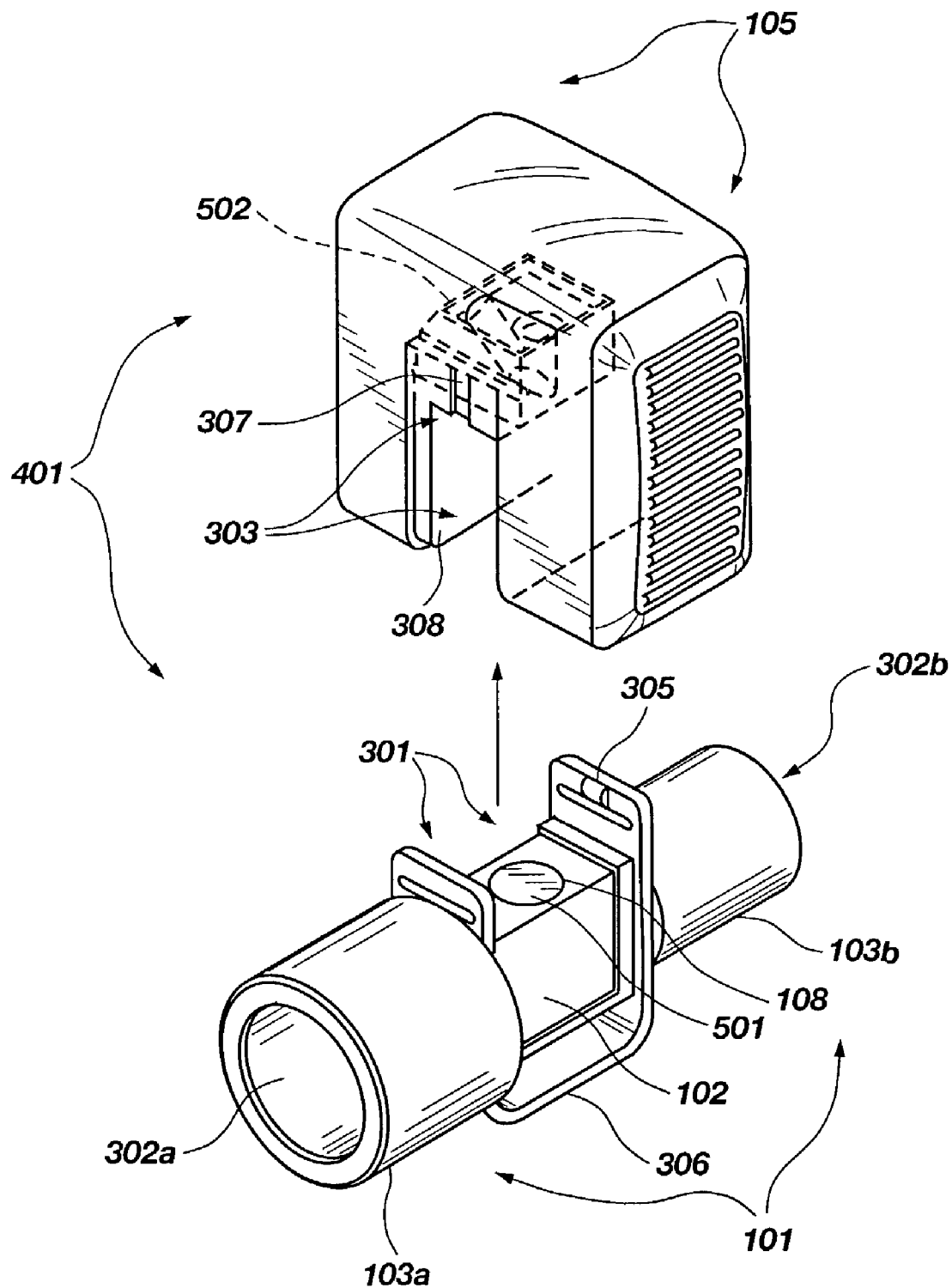
FIG. 5 is a perspective view of an alternative airway adapter and a complementary transducer that shows the relationship of an optical block assembly to the airway adapter.

FIG. 5 illustrates another embodiment of two-piece assembly 401. Airway adapter 101 includes the three sections 103a, 301, and 103b that together form an inline gas flow passage 302a, 102, and 302b. Center section 301 of inline airway adapter 101 is formed to fit snugly into corresponding section 303 of transducer 105. Stops 305 and 306 on airway adapter 101 are formed so as to create a snug fit with corresponding stops 307 and 308, respectively, when inline airway adapter 101 is coupled to transducer 105. Aperture 108, formed in a side of airway adapter center section 301, contains a window 501. Window 501 supports sensing film 104 (not shown) within sensing volume 102 and provides a thermal energy transmission path from a temperature regulation apparatus 114 (see FIG. 1) housed within transducer 105.

Transducer 105 contains an optical block assembly 502. Optical block assembly 502 contains the light source 106 and photodetector 110 (see FIG. 1) in proper alignment. Optical block assembly 502 also houses a heater assembly 114 (not shown) for maintaining a constant temperature within sensing film 104 (not shown). The use of an optical block assembly 502 as a subassembly aids in the manufacturability of the transducer 105. By containing all critical alignments and tolerances associated with transducer 105 within optical block assembly 502, the manufacturing tolerances of the outer housing of transducer 105 may be loosened somewhat, thus reducing cost. Furthermore, service related to failure of one or more components within the optical block assembly 502 may be treated as a subassembly level repair, rather than forcing a replacement of the entire transducer assembly 105.

Figure 6:
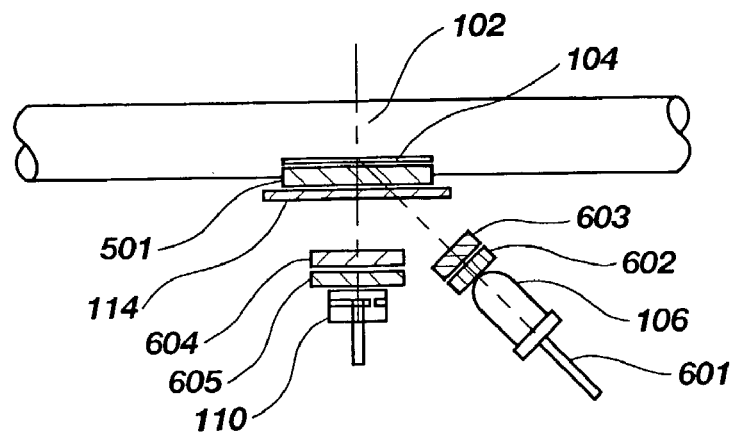
FIG. 6 is a diagram showing the optical alignment of key optical components of a transducer and sampling cuvette of the present invention in a "single-sided" arrangement.

FIG. 6 is a conceptual diagram of the main optical components of an embodiment of the present invention. Light emitting diode (LED) 106 emits blue or green light in response to an energization signal transmitted via leads 601. The blue or green light passes through dichroic filter 602 and infrared-blocking filter 603. In the embodiment illustrated in FIG. 6, the light energy then passes through an aperture in heater 114, through window 501, and falls upon sensing film 104. Sensing film 104 is held in intimate contact with window 501 by any of a number of methods, such as adhesive or solvent bonding, or via a retaining ring or mesh covering. This allows the sensing film 104 to freely contact the gas within sensing volume 102.

LEDs are known to generally emit a relatively broad range of light wavelengths extending to some degree even into the infrared. The dichroic filter 602 and infrared-blocking filter 603 cooperate to significantly reduce wavelengths other than the narrow range of wavelengths passed by the dichroic filter. The particular wavelength chosen for passage by the dichroic filter 602 may be selected to correspond to the peak output of LED 106 and to a suitable energization wavelength for the sensing film 104. In a preferred embodiment, this wavelength is chosen to be in the blue range of the visible electromagnetic spectrum.

Energization light incident upon sensing film 104 causes the film to begin to emit light of a different wavelength. The sensing film may be comprised, for instance, of a microporous polycarbonate film having a platinum-porphyrin dye contained therein as in a guest-host system. The microporosity of the film represents a novel approach in the preparation of films designed for the monitoring of gaseous oxygen concentrations. The preparation of the polymeric membrane is well known in the art of manufacturing microporous screens and will not be described in detail herein. Suffice it to say that the process involves two steps wherein the polymer film is exposed to collimated, charged particles in a nuclear reactor which pass through the polymer, leaving behind sensitized tracks which are then etched into uniform cylindrical pores. The incorporation of the luminescent sensing material into the film is more fully described in co-pending U.S. patent application entitled "Oxygen Monitoring Methods and Apparatus" having Ser. No. 09/128,897, hereby incorporated herein in its entirety by this reference.

In one embodiment of the present invention, the emission wavelength of the sensing film 104 corresponds to light in the red portion of the visible electromagnetic spectrum. An LED 106 is repeatedly pulsed at a frequency of 20 kilohertz with its output excitation energy 107 rising and falling as a sinusoidal wave. This causes a rise and fall in luminescence energy emitted from the sensing film 104 that is a function of oxygen concentration in sensing volume 102. The effect of a single pulse is qualitatively illustrated in FIG. 2.

Luminescence emitted by sensing film 104 passes through window 501, through an aperture in heater 114, through red dichroic filter 604, through red filter 605, and impinges upon photodetector 110. Red filter 605 may be comprised of a conventional glass or gel filter. Red dichroic filter 604 and red filter 605 cooperate to virtually eliminate any light emitted by LED 106 through dichroic filter 602 and infrared-blocking filter 603 from reaching photodetector 110. The geometric relationship of emitter and detector field-of-views further serves to reduce the amount of excitation energy reaching photodetector 110 arising, for instance, from specular reflection off a surface of window 501.

Heater 114 is maintained in intimate contact with window 501 so as to maximize the effectiveness of the energy conduction path from heater 114 through window 501 into sensing film 104. Maintaining a constant temperature within sensing film 104 is advantageous for keeping the relationship between oxygen concentration within sensing volume 102 and the amount of luminescence-quenching sensed by photodetector 110 constant. Window 501 is preferably comprised of a material having relatively high thermal conductivity and high transparency such as sapphire, glass, quartz, polycarbonate, or other material apparent to those skilled in the art. Window 501 should be constructed so as to maximize transmission of excitation energy and especially to maximize transmission of luminescence energy. The materials listed above also accomplish this aim. Furthermore, it is advantageous to maintain the temperature of the sensing film 104 and window 501 somewhat above the temperature of the gas in sensing volume 102. This serves to avoid condensation of vapors on the window, which may otherwise obscure the window and reduce the effectiveness of the sensing apparatus.

Figure 7:
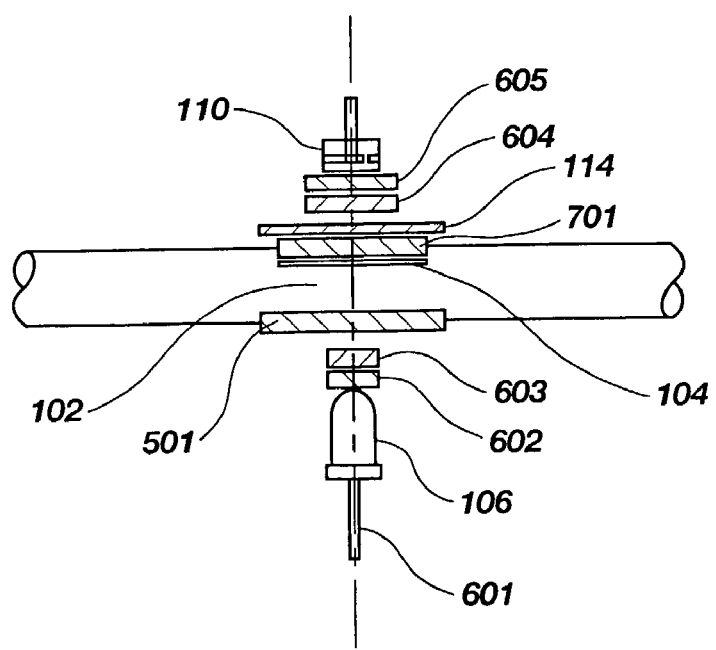
FIGS. 7 and 8 are diagrams showing the relationship of the optical components in "straight-through" and "two-sided" arrangements respectively, as disclosed in a prior copending application.
Figure 8:
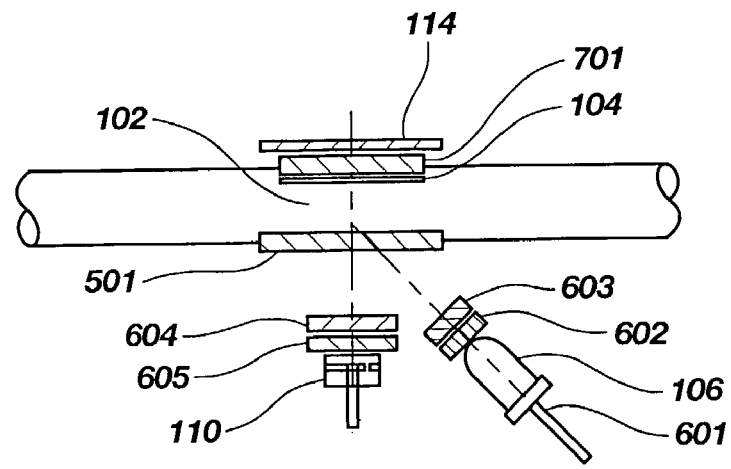

The arrangement of emitter, detector, filters, and sensing film described by FIG. 6 is particularly effective at maximizing the signal-to-noise ratio of the detection apparatus of the present invention. The arrangement of electrical components shown in FIG. 6 on one side of sensing volume 102 serves to reduce cost and improve reliability compared to other arrangements wherein electrical components are arrayed on opposing sides of sensing volume 102. FIGS. 7 and 8 illustrate configurations of the optical components representative of such arrangements and of those disclosed in co-pending application Ser. No. 09/128,918.

Figure 9:
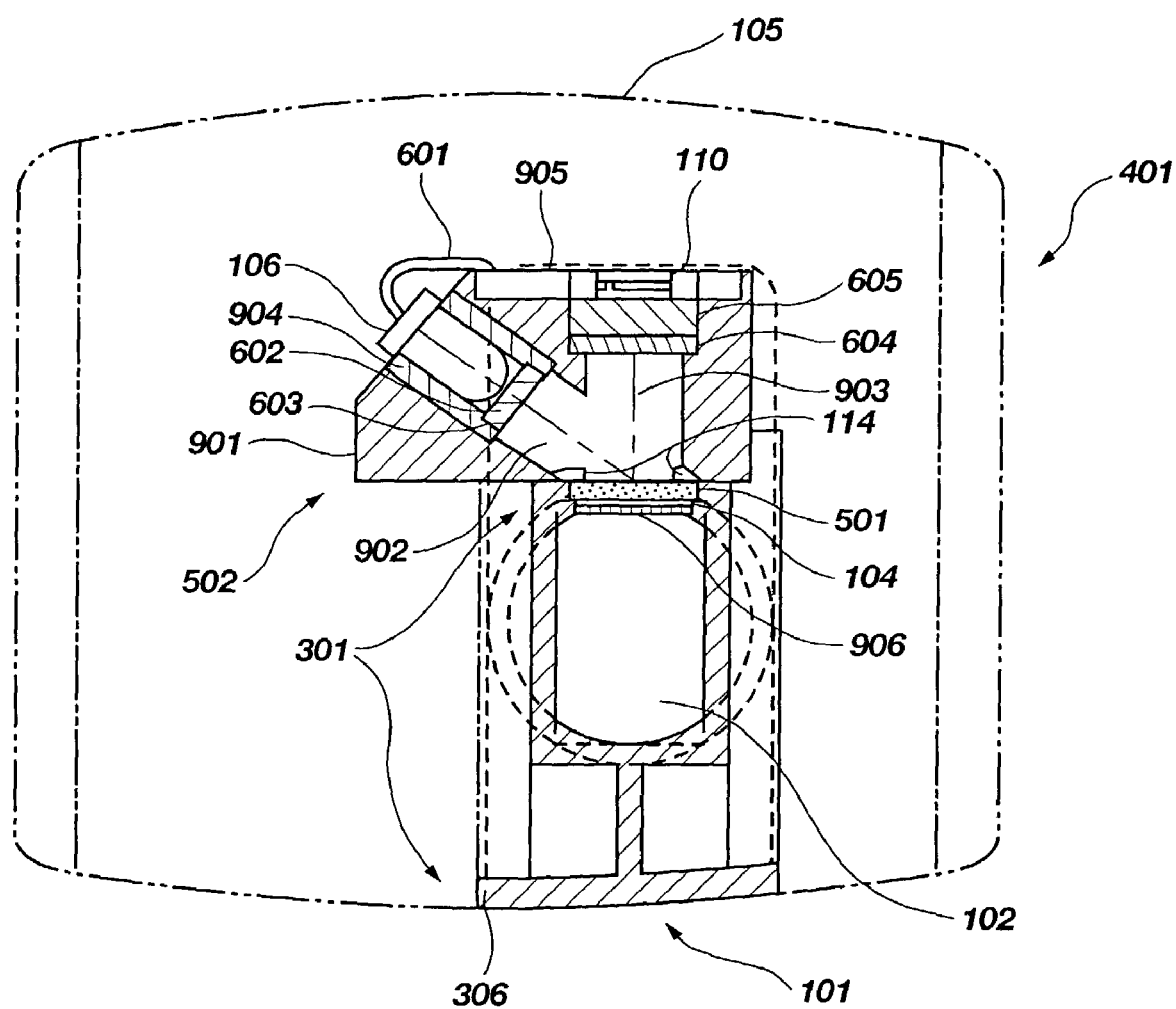
FIG. 9 is a cross-sectional view of the airway adapter and transducer assembly of FIG. 5 showing the spatial relationship of key optical components in the optical block assembly.

Turning our attention now to FIG. 9, a cross-sectional view of two-component assembly is illustrated generally at 401 showing especially the means for optical alignment of key components. The arrangement of components correlates most closely to the embodiment depicted in FIG. 6 in accordance with the principles of the present invention. The center section 301 of inline airway adapter 101 is held in place within transducer housing 105. Center section 301 of the inline airway adapter 101 is held in correct optical alignment with optical block assembly 502 by means of the close fit between stop features 306 and 308 (not shown) and between the outer walls of airway adapter 101 and the inner walls of the transducer body 105 as illustrated by FIGS. 3 and 5.

Optical block assembly 502 is comprised of an optical block casing or body 901 that holds key optical components in boresight alignment by means of two bores created therein, light source bore 902 and detector bore 903, each of which is aligned to hold their respective components so as to create substantially coincident fields of view of sensing film 104. LED 106 and filters 602 and 603 are held in LED mounting tube 904. LED mounting tube 904 may be constructed of brass tubing or other appropriate material. LED mounting tube 904 is coupled to light source bore 902 and holds the LED and filters for illuminating the sensing film 104. LED 106 receives a signal via leads 601 from optical block circuit board 905. In another embodiment, LED 106 receives a signal through leads 601 from optical block circuit board 905. Optical block circuit board 905 further provides means for mounting photodetector 110 and holding it aligned with detector bore 903. Light emitted from sensing film 104 thus passes through window 501, traverses detector bore 903, passes through red dichroic filter 604 and red filter 605, and impinges upon photodetector 110. In a preferred embodiment, photodetector 110 is comprised of a photodiode.

Heater 114 is shown in cross-section with its aperture therethrough allowing passage of both excitation energy and luminescent emission. Parts of heater 114 peripheral to the aperture are held in intimate contact with window 501. Sensing film 104 is maintained in intimate contact with window 501 by optional porous member 906 or by other means as described previously. Porous member 906 may be comprised of any material that allows free passage of the gas in sensing volume 102 to sensing film 104 and has appropriate tensile strength and heat-resistance properties. In practice, it has been found that it is especially advantageous for porous member 906 to be comprised of a stainless steel screen. In this embodiment, heat conduction along the wires of stainless steel screen 906 aids in the control and maintenance of the temperature of sensing film 104.

Figure 10:
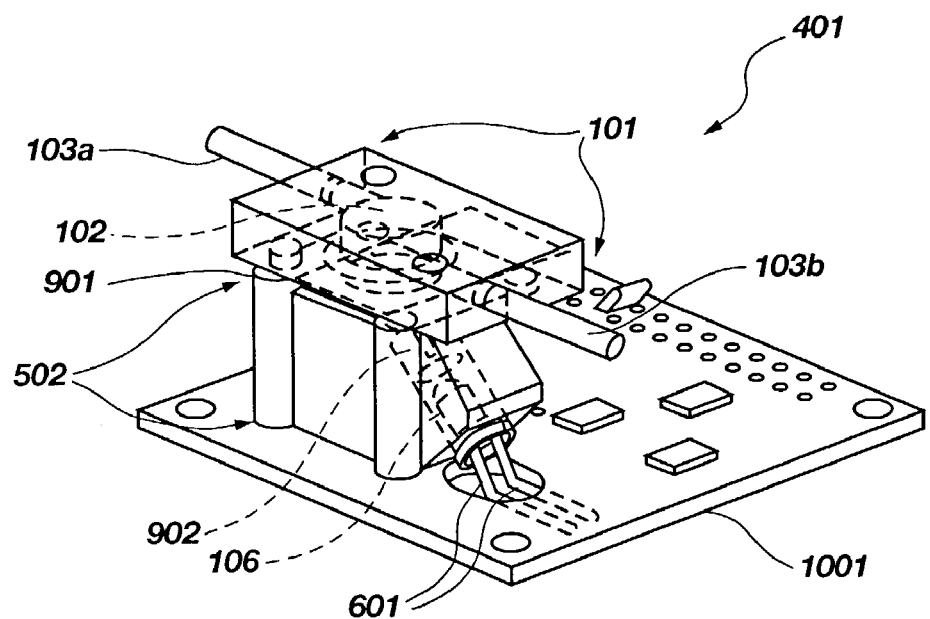
FIG. 10 shows a perspective view of a sidestream embodiment of the present invention.

FIG. 10 shows a perspective view of a sidestream embodiment of the present invention. Circuit board 1001 supports an optical block assembly 502. A sampling cuvette 101 containing a sampling volume 102 and inlet/outlet ports 103a and 103b is affixed to the optical block with machine screws (not shown) or by other means known in the art. Optical block 502 also includes a light source bore 902 which contains LED 106. LED 106 is, in turn, connected to circuit board 1001 and the circuit thereon by means of leads 601.

The cuvette 101 may be made from machined and anodized aluminum with ports 103a and 103b press-fit therein. Optical block casing 901 may be similarly constructed from machined and anodized aluminum.

Circuit board 1001 may contain all or part of control and measurement circuitry in addition to providing a mounting point for optical block assembly 502. In some embodiments, circuit board 1001 may be mounted inside diagnostic equipment such as an anesthesia monitor and provide connections 113 (not shown) to such equipment.

Figure 11:
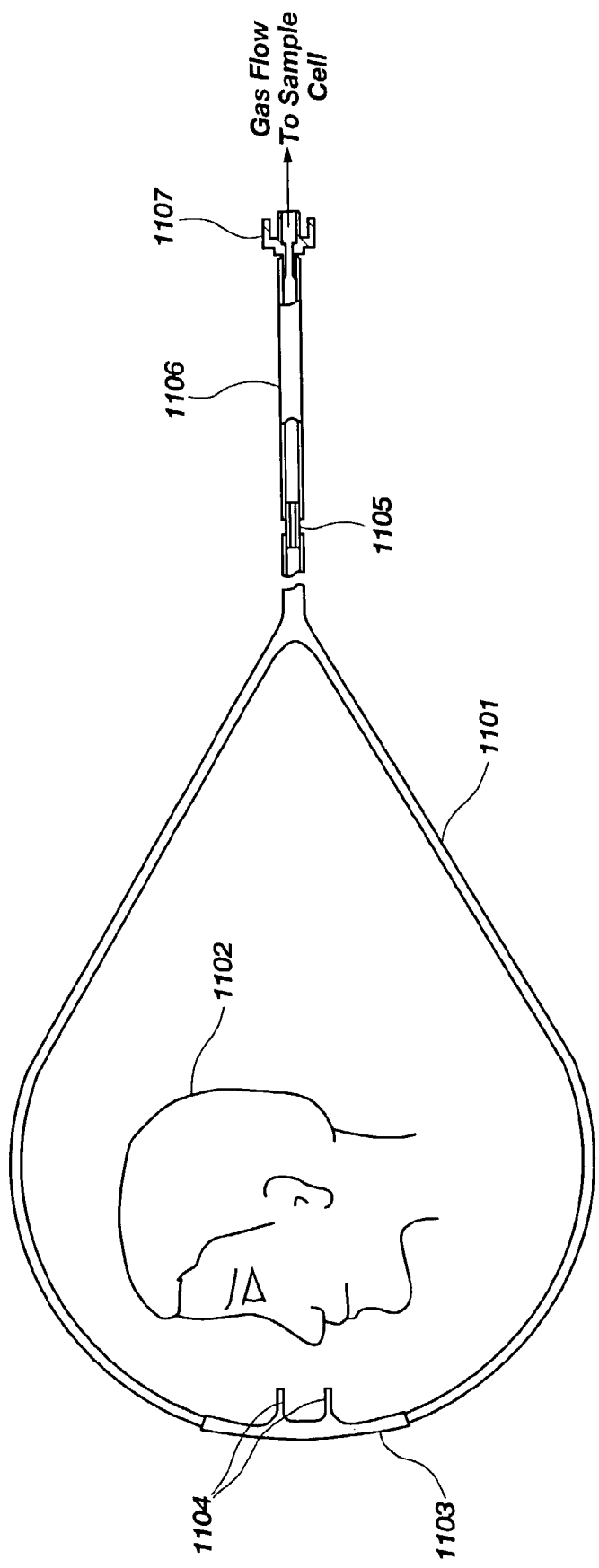
FIG. 11 illustrates a nasal canula component for sampling a patient's respiratory gases for subsequent monitoring by a sidestream monitor such as that shown in FIG. 10.

FIG. 11 illustrates a nasal canula component which may be employed to sample a patient's respiratory gases for subsequent monitoring by a sidestream monitor such as that shown in FIG. 10. The nasal canula of FIG. 11 is of the conventional type typically found in hospitals or other health care facilities. It includes tubing 1101 that fits over the head of a patient 1102. An insert 1103 in the tubing features a pair of protruding tube-shaped members 1104 that fit into the patient's nostrils. The nasal canula is connected as by tubular fitting 1105 to a flexible Nafine drying tube 1106. The drying tube removes moisture from gases exhaled by patient 1102, thereby eliminating errors that moisture might cause. At the far end of the Nafine drying tube 1106 is the female component 1107 of a conventional Leur fitting. A male Leur fitting (not shown) may be connected to a gas sampling tube (not shown) and transmitted to a sidestream oxygen sensing device such as that of FIG. 10 by means of a pump (not shown) such as a peristaltic pump.

Figure 12:
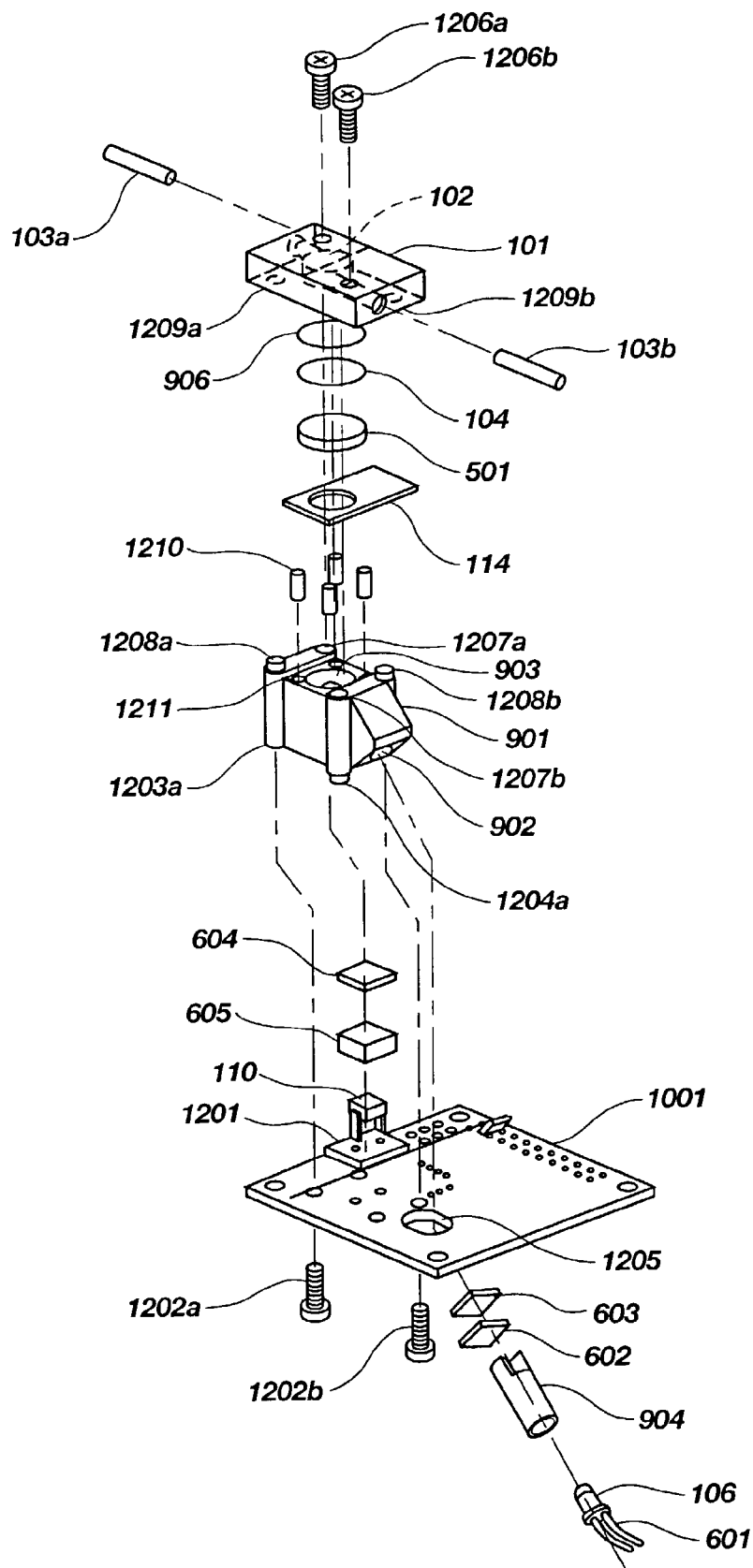
FIG. 12 depicts an exploded view of the sidestream embodiment shown in perspective in FIG. 10 showing pertinent details of device assembly.

FIG. 12 shows an exploded view of the sidestream gas measurement device illustrated in FIG. 10. Photodetector 110, in the form of a photodiode, is mounted through holes in photodiode mounting block 1201 to circuit board 1001 and thus connected into the circuit thereon. Photodiode mounting block 1201 is itself glued to the surface of circuit board 1001 in order to hold photodetector 110 at the correct height in detector bore 903, which is formed in optical block body 901. Filters 604 and 605 are mounted into the detector bore 903 of optical block body 901 in the manner indicated. Optical block body 901 is affixed to circuit board 1001 using optical block mounting screws 1202a and 1202b which extend through holes in circuit board 1001 into tapped holes 1203 (only one hole, 1203a, is indicated for clarity) formed diagonally across detector bore 903 in optical block body 901. Optical block locating stops 1204a and 1204b (not shown) are located on the opposite diagonal of detector bore 903 to optical block mounting screws 1202a and 1202b and extend into holes formed in circuit board 1001 for aiding the proper location of optical block body 901.

LED mounting tube 904 extends into light source bore 902 in optical block body 901 and is held therein via a press fit, trapping dichroic filter 602 and infrared blocking-filter 603 against a shoulder formed within the light source bore. An optional diffuser may be inserted between dichroic filter 602 and LED 106 for reducing hot spots in the LED emission pattern. LED 106 is held inside LED mounting tube 904 using a press fit, adhesive mounting, or any suitable alternative mounting method. LED leads 601 extend through an aperture 1205 formed in circuit board 1001 and are soldered to traces on the bottom of the circuit board 1001.

Cuvette 101 is coupled to optical block body 901 with gas sensing volume 102 registered on axis to detector bore 903 using two screws 1206a and 1206b extending through corresponding holes in cuvette 101 formed diagonally to gas measurement volume 102. Screws 1206a and 1206b couple into corresponding tapped holes 1207a and 1207b, respectively, formed in optical block body 901. Ports 103a and 103b are inserted into cuvette 101 and may be attached via screws, press fitting, or adhesive, or may be formed integrally into the cuvette body, or may be held in place using other means apparent to one skilled in the art. Stops 1208a and 1208b formed in optical block body 901 extend into corresponding holes 1209a and 1209b formed in cuvette 101 at an opposite diagonal to screws 1206a and 1206b relative to detector bore 903 and sensing volume 102. Stops 1208a and 1208b and their corresponding holes 1209a and 1209b aid in locating the cuvette relative to the optical block body 901 and are especially useful during assembly. The cuvette body may be constructed of machined aluminum, machined stainless steel, die cast metal, molded plastic, or other suitable material.

Porous member 906, sensing film 104, and window. 501 are captivated on a shoulder formed circumferentially to gas sensing volume 102 in cuvette 101. These may be affixed by press fit or may be affixed in place using silicone adhesive or other alternative means apparent to those skilled in the art. Window 501 may be comprised of sapphire, glass, quartz, plastic or other material. Materials for window 501 may be chosen for their combination of high transparency at excitation and emission wavelengths as well as high thermal conductivity and low thermal mass. Heater 114 is urged into intimate contact with window 501 by heater springs 1210 which extend into corresponding holes 1211 formed in optical block body 901. In one embodiment, heater 114 is a ceramic heater with integral thermister. The use of springs 1210 to hold heater 114 against window 501 helps to eliminate point loading and/or tight tolerance requirements on heater 114 and the corresponding gap between cuvette 101 and optical block body 901. For the case where heater 114 is formed of ceramic or other brittle material, this arrangement also serves to reduce heater breakage during assembly and during service. In one embodiment, springs 1210 may be formed from silicone rubber.

Figure 13:
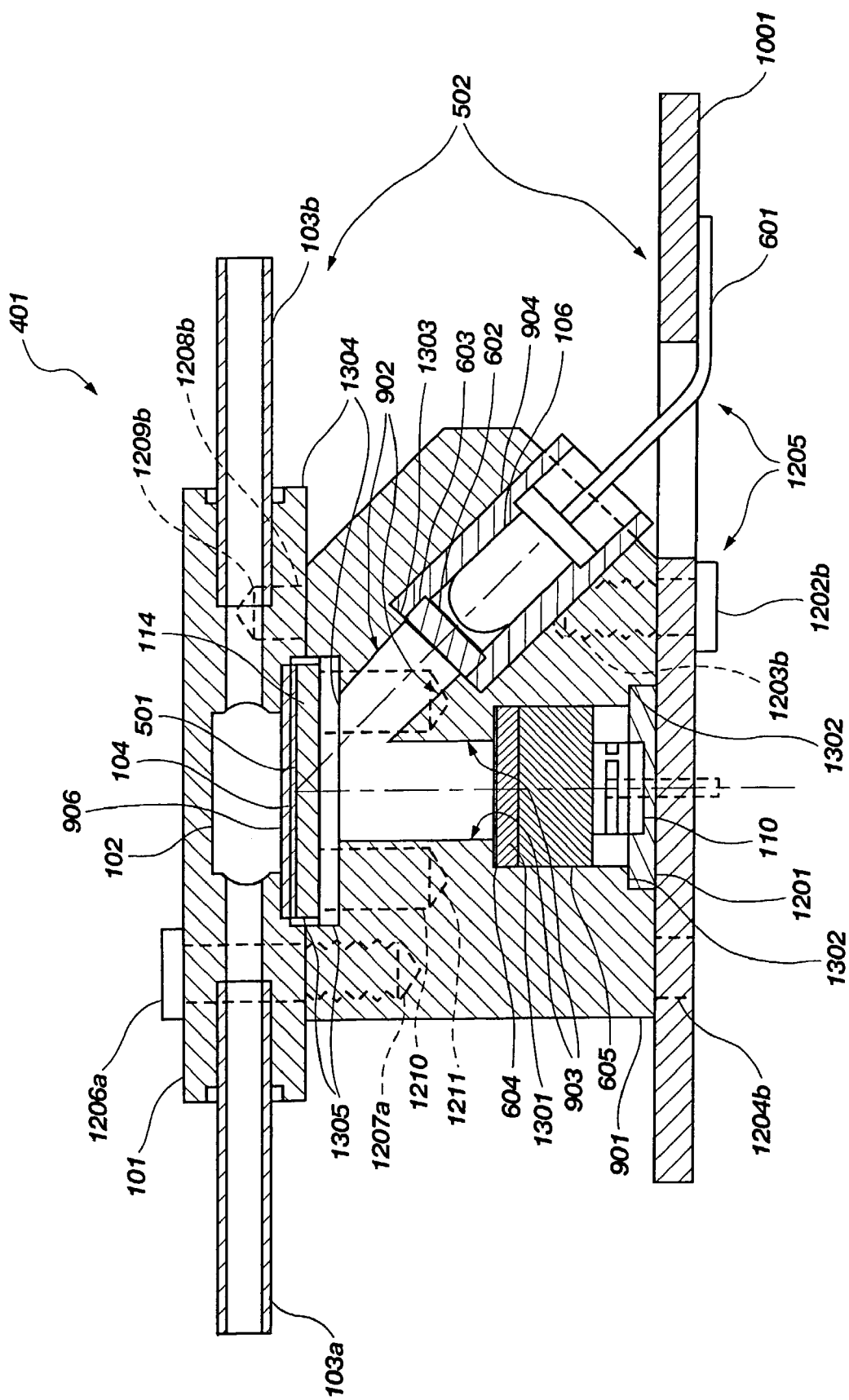
FIG. 13 is a cross-sectional view of the sidestream gas measurement system of FIGS. 10 and 12 showing especially details of optical alignment and heater-to-sensing film relationship.

Referring now to FIG. 13, a cross-sectional view of the sidestream gas measurement system of FIGS. 10 and 12 is shown. Detector bore 903 in optical block body 901 has two shoulders 1301 and 1302 formed circumferentially at the bottom of the bore 903. Shoulder 1301 serves as a stop for locating of the top of red dichroic filter 604. Shoulder 1302 serves as a stop for locating the top of photodiode mounting block 1201. Photodetector 110 is supported on photodiode mounting block 1201 and presses up against red filter 605. Red filter 605, in turn, presses against the bottom of red dichroic filter 604 and urges it against shoulder 1301 in detector bore 903. When circuit board 1001 is affixed to optical block body 901 using screws 1202a (not shown) and 1202b, photodiode mounting block 1201 is urged against shoulder 1302 in detector bore 903. Photodiode mounting block 1201 also presses the assembly comprising photodetector 110, red filter 605, and red dichroic filter 604 against shoulder 1301 in the detector bore 903. In this way, when optical block body 901 is affixed to circuit board 1001, the entire detector assembly is securely coupled to its correct location in the optical block body.

Light source bore 902 has one shoulder 1303 formed therein for locating the end of LED mounting tube 904. Shoulder 1303 furthermore serves to locate the top of infrared-blocking filter 603. When LED mounting tube 904 is pressed into emitter bore 902 of optical block body 901, it pushes against the bottom of dichroic filter 602, urging it up into its correct location above LED 106. The top of dichroic filter 602, in turn, presses against the bottom of infrared-blocking filter 603, which itself is urged against shoulder 1303 in light source bore 902. In this way, the proper insertion of LED mounting tube 904, with LED 106 held therein, in light source bore 902 captures the entire light source assembly comprising the LED 106, dichroic filter 602, and infrared blocking filter 603 at its correct position in optical block body 901.

LED mounting tube 904 and the rest of the light source assembly may be inserted into the light source bore 902 of optical block body 901 through aperture 1205 in circuit board 1001 after securely affixing the optical block body 901 to the circuit board using screws 1202a and 1202b. Alternatively, the light source assembly may be inserted into the light source bore 902 prior to attaching the optical block body 901 to circuit board 1001. In either case, LED leads 601 may be subsequently bent into position contacting their corresponding electrical traces (not shown) on circuit board 1001 and soldered thereto. Alternatively, other types of socketed connectors may be used to receive LED leads 601 or their equivalent or other types of permanent connection may be made.

Cuvette body 101 has a shoulder 1305 formed circumferentially to the bottom aperture of gas sensing volume 102. Shoulder 1305 serves as a location feature for locating the sensor and window assembly comprising porous member 906, sensing film 104, and window 501 relative to gas sensing volume 102. Optical block body 901 has a depressed planar area 1304 corresponding to and extending beyond shoulder 1305 formed between cuvette mounting surfaces. This serves to provide a volume for accepting heater 114 and any protruding thickness of window 501. Four heater spring holes 1211 extend from planar area 1304 into the volume of optical block body 901. Four heater springs 1210 are inserted into heater spring holes 1211 prior to placing heater 114 thereon with its aperture located axially along detector bore 903. Cuvette 101 with the sensor and window assembly seated therein is placed over heater 114 and located with window 501 aligned axially to detector bore 903. Stops 1208a (see FIG. 12) and 1208b formed in optical block body 901 extend into holes 1209a (see FIG. 12) and 1209b, respectively, formed in cuvette 101. Stops 1208a and 1208b and their corresponding holes 1209a and 1209b aid in the alignment of window 501, sensing film 104, porous member 906, and gas sampling volume 102 to the detector bore 903 formed in the optical block body 901 during assembly and service. As cuvette mounting screws 1206a and 1206b are tightened, heater springs 1210 compress in their holes 1211 and urge heater 114 against the bottom of window 501. This upward pressure on window 501 further compresses sensing film 104 and porous member 906 against shoulder 1305 in sensing volume 102 of cuvette 101. As screws 1206a and 1206b are torqued to predetermined values, the bottom of cuvette 101 comes into close coupling with the top surface of optical block body 901. Thus the use of heater springs 1210 to compress the assembly comprising heater 114, window 501, sensing film 104, and porous member 906 against shoulder 1305 causes the entire sensor and window assembly to be brought into correct optical alignment with other components of optical block assembly 502 when cuvette 101 is properly coupled against optical block body 901.

Figure 14:
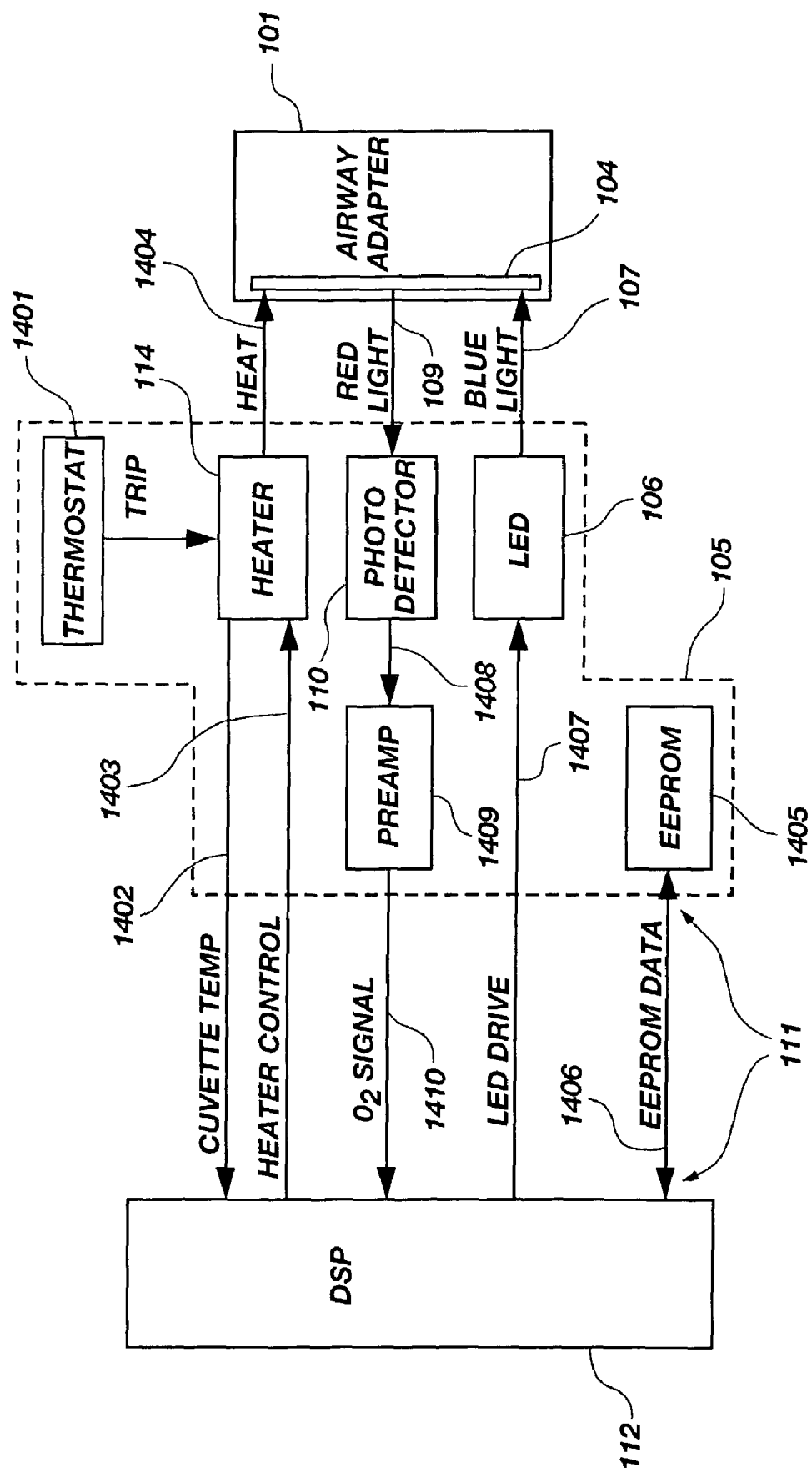
FIG. 14 is a block diagram of a DSP-based controller that is especially well adapted for a mainstream embodiment of the invention.

FIG. 14 is a block diagram of a controller for controlling the gas measurement apparatus of the present invention and for receiving data that may be converted to gas concentration information. The controller of FIG. 14 is particularly applicable to a mainstream gas analyzer such as that depicted by FIGS. 3 through 5.

The main assemblies shown in FIG. 14 include a controller corresponding to circuitry and display 112 from FIG. 1, transducer 105, and cuvette or airway adapter 101 containing sensing film 104. Transducer 105 contains LED 106, photodetector 110, and heater 114, and additionally a thermostat 1401, a memory 1405, and a photodetector pre-amp 1409.

Control and electrical connections 111 connect control and measurement circuitry 112 to transducer 105 and include cuvette temperature signal 1402, heater control line or signal 1403, data line 1406, LED drive 1407, and oxygen signal 1410. Excitation light 107, luminescence light 109, and heat conduction path 1404 form the interface between transducer 105 and airway adapter 101.

Digital Signal Processing (DSP) controller 112 may, for example, contain control and detection circuitry as well as communications circuitry and logic for communicating with a host computer and/or for displaying gas concentration measurement data to the user. One aspect of system operation controlled by DSP controller 112 is the temperature of the sensing film 104.

Heater 114 may contain an integral thermostat 1401 or, alternatively, may contain a separate thermostat 1401. In any event, heater 114 may preferably contain a circuit to cut heater drive in the event of heater control failure. Thermostat 1401 and associated heater cutoff circuit serves as a fail-safe device to avoid runaway heater drive and a resultant possibly unsafe situation or destruction of sensing film 104. Cuvette temperature is transmitted to the DSP controller circuit by an analog signal 1402, the voltage of which is proportional to the temperature of heater 114 and, by extension, the temperature of sensing film 104. Analog cuvette temperature signal 1402 may, for instance, be generated by a thermistor integral to or otherwise coupled to heater 114 or, alternatively, coupled to a convenient location whose temperature varies proportionally to the temperature of heater 114. Heater control signal 1403 is driven from DSP controller 112 as a pulse width modulated (PWM) digital control signal whose duty cycle is controlled by a fuzzy logic controller embedded within DSP controller 112. The fuzzy logic portion of the DSP controller is programmed in a manner similar to a proportional integral-differential (PID) controller. Fuzzy logic embedded in the DSP controller 112 monitors the analog cuvette temperature signal 1402 via an analog-to-digital (A/D) converter and controls the duty cycle of PWM heater control signal 1403 in response. The duty cycle of heater control signal 1403 is controlled to be higher when the cuvette temperature is cooler and controlled to be lower when the cuvette temperature is warmer. In practice, this control methodology may be used to maintain a constant temperature in sensing film 104. Heater control signal 1403 drives a transistor (not shown) that may, for instance, be integral to heater 114. The transistor driven by PWM heater control signal 1403 acts as a relay that switches drive current to heater 114 on or off. Heat flows from heater 114 to sensing film 104 via a heat conduction path 1404. By setting the temperature of sensing film 104 above that of the flowing gas to be sensed, heat always flows from the heater 114 to the sensing film. The amount of heat modulated by heater control signal 1402 thus may always act as a positive control signal, heat never needing to be removed from the system.

Memory element 1405, which may, for instance, be embodied as electrically erasable programmable read-only memory (EEPROM) or flash memory, is associated with a transducer 105. Memory 1405 contains a transducer serial number and calibration information indicating oxygen concentration vs. phase shift. At boot-up, controller 112 reads the transducer serial number from memory 1405 to determine if proper calibration information has been loaded. If the transducer 105 is the same unit that had been connected to DSP controller 112 during its previous operational session, no further data is read from memory 1405 and boot-up continues. If the serial number encoded within memory 1405 indicates that transducer 105 is a new pairing with DSP controller 112, calibration data and the serial number is read from memory 1405 and written in non-volatile form into memory (not shown) contained within DSP controller 112. Upon subsequent boot-ups with the same transducer 105, this previously stored calibration data is used directly.

During operation, controller 112 drives LED 106 with a phase angle modulated signal via LED drive 1407. Light energy 107 emitted from LED 106 is pulsed onto sensing film 104 with phase angle modulation corresponding to the LED drive signal 1407. In a preferred embodiment, excitation energy 107 emitted from LED 106 has a spectral distribution predominantly in the blue portion of the electromagnetic spectrum and serves to excite sensing film 104 into luminescence. Photodetector 110 transforms luminescence into a current- or voltage-modulated electrical signal 1408 which, in turn, is amplified to a usable oxygen signal 1410 by pre-amplifier 1409. Pre-amplifier 1409 may be, for instance, a low noise operational amplifier. Oxygen signal 1410 is transmitted to DSP controller 112 via a conventional conductive wire where it is used to determine oxygen concentration within airway adapter 101.

The oxygen signal 1410 may be a function of several factors in addition to oxygen concentration including pre-amp 1409 characteristics, photodetector 110 characteristics, and other detector optical idiosyncrasies. Luminescent energy 109 emitted from sensing film 104 has a temporal intensity curve (similar to curves shown in FIG. 2) related to excitation energy 107 received from LED 106, sensing film temperature, oxygen concentration within airway adapter 101, and possibly the amount of previous photo-degradation of sensing film 104. The particular amount and quality of excitation energy 107 emitted by LED 106 varies according to LED output efficiency and spatial distribution, variations in alignment and transmissivity of the particular components of the transducer emitter assembly as well as the phase angle modulated signal input via LED drive 1407.

The effects of factors other than oxygen concentration and LED drive signal may, to a great extent, be eliminated, thus simplifying the problem of determining concentration. Transducer-specific factors such as pre-amp characteristics, detector assembly characteristics, variations in heater calibration, variations in overall LED output efficiency, and other alignment variations may be eliminated from consideration by use of the transducer-specific calibration data contained within memory 1405 according to the method described above. Variations in sensing film oxygen diffusivity (as a function of temperature) may be eliminated by keeping the sensing film 104 at a constant temperature using methods described above. Deleterious effects due to sensing film photo-degradation may be largely eliminated by packaging the sensing film 104 as a part of a disposable airway adapter 101, thus ensuring that the sensing film is always fresh. Thus, the problem of determining oxygen concentration is simplified to comparing the oxygen signal 1410 to the phase angle modulated LED drive signal 1407.

Figure 15:
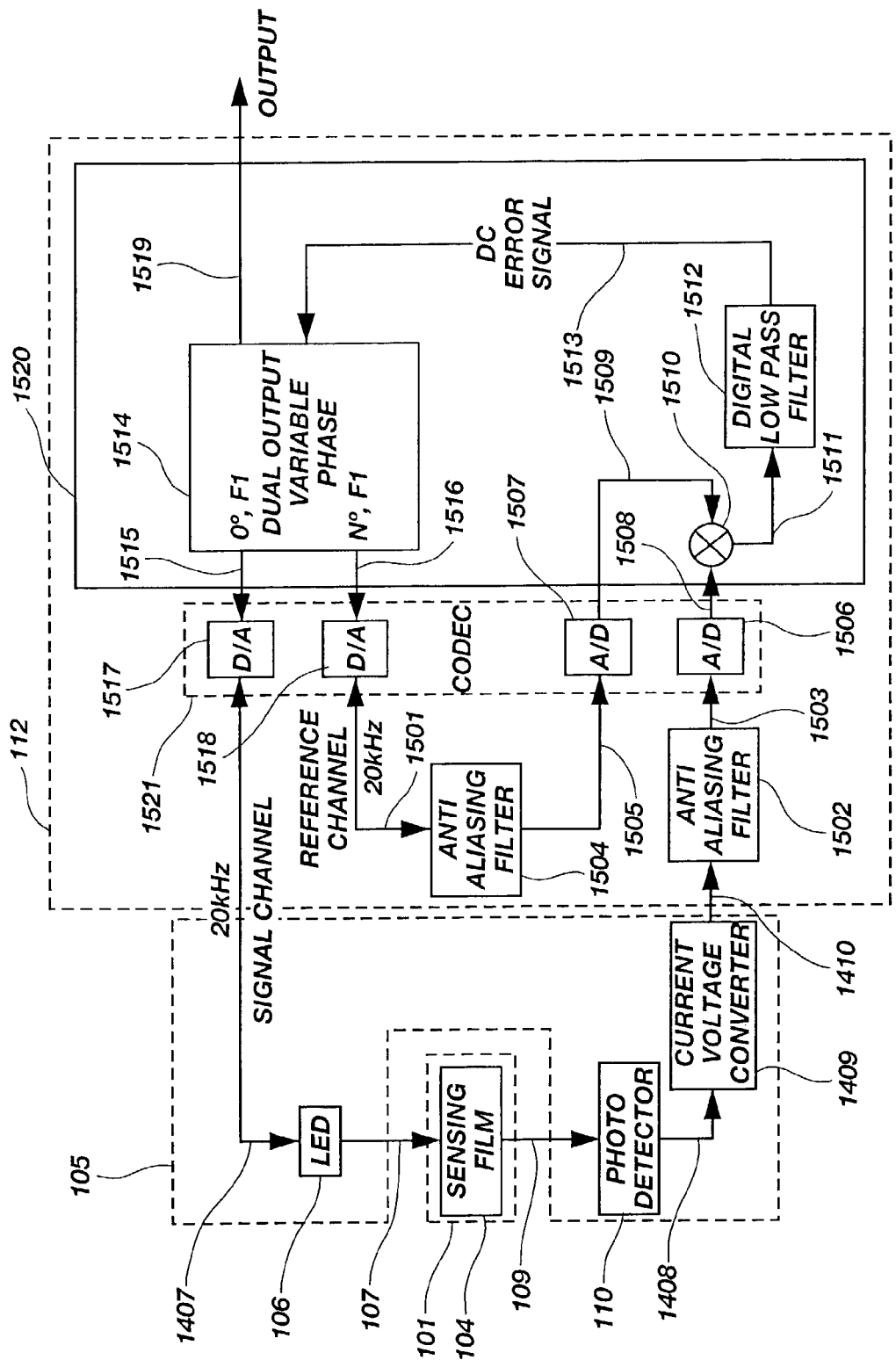
FIG. 15 is a block diagram that describes more specifically the methodology for determining oxygen concentration from the luminescence characteristics of a sensing film.

FIG. 15 is a block diagram that describes more specifically the process of comparing the LED drive signal 1407 to the oxygen signal 1410 to determine oxygen concentration. A portion of the DSP controller 112 is shown with connections to the transducer 105 comprising an LED drive 1407 and an oxygen signal 1410. The memory heater and thermostat, as well as their corresponding connections are omitted from FIG. 15 for the sake of clarity. DSP integrated circuit 1520 forms the heart of processing functionality and CODEC 1521 provides analog/digital interfaces on DSP controller 112. Current voltage converter 1409 corresponds to pre-amp 1409 in FIG. 14 and is indicative of one embodiment. As described in conjunction with FIG. 14, LED drive 1407 pulses LED 106 which emits a corresponding excitation energy 107 to excite luminescence in fluorescent sample 104. Upon receiving a pulse of excitation energy 107, sensing film 104 emits luminescence energy 109 with an intensity and duration inversely proportional to oxygen concentration in the sampling volume 102 (not shown) of the airway adapter 101, as shown by FIG. 2. Photodetector 110 converts variations in luminescence 109 to corresponding variations in electrical signal 1408 that current voltage converter 1409, in turn, amplifies and converts to variations in voltage prior to transmitting the resultant oxygen signal.1410 back to the DSP controller 112. Signals 109, 1408, and 1410 thus are effectively phase-retarded output signals with the amount of phase retardation determined by oxygen concentration.

For the purposes of the signal processing to be done, transducer 105 may be considered a trans-impedance amplifier. LED drive 1407 and reference channel 1501 are driven as pure sine waves. Due to perturbations introduced by sensing film 104, oxygen signal 1410 is modified somewhat from the pure sine wave of LED drive 1407. The perturbations introduced by sensing film 104 are, of course, the very signal from which oxygen concentration may be derived.

Oxygen signal 1410 is passed to DSP controller 112 and sent through anti-aliasing filter 1502 to remove phase delays relative to LED drive 1407 introduced by propagation delays along the signal path length, thus producing anti-aliased oxygen signal 1503. Reference channel 1501, nominally driven in quadrature to LED drive 1407, is similarly passed through anti-aliasing filter 1504 to produce anti-aliased reference signal 1505.

Anti-aliased oxygen signal 1503 and anti-aliased reference signal 1505 are converted to digital signals by passing through analog-to-digital (A/D) converter channels 1506 and 1507, respectively. Digital oxygen signal 1508 and digital reference signal 1509, which result from the A/D conversion, are then mixed by mixer 1510 to create AC coupled error signal 1511. Digital mixer 1510 multiplies signals 1508 and 1509 point-by-point to produce error signal 1511. AC coupled error signal 1511 is subsequently processed by digital low pass filter 1512 to remove the AC coupling and produce DC error signal 1513. DC error signal 1513 has a voltage proportional to the signal perturbations (phase delay) introduced by the luminescence-quenching oxygen measurement sensing film 104 in converting LED drive signal 1407 to oxygen signal 1410. Less phase delay in the signal channel relative to the reference channel, corresponding to higher oxygen concentrations, results in a lower DC error signal 1513. Conversely, greater phase delay in the signal channel relative to the reference channel corresponds to lower oxygen concentration and a higher DC error signal 1513.

Dual output variable phase drive 1514 outputs digital waveforms along channels 1515 and 1516 which are converted by digital-to-analog (D/A) converter channels 1517 and 1518, respectively, to create LED drive 1407 and reference channel 1501, respectively. Frequency is held constant by drive 1514 while the phase of the two channels 1517 and 1518 is varied relative to one another. Specifically, drive 1514 advances the phase of digital reference channel 1516 in response to DC error signal 1513 to minimize the magnitude of DC error signal 1513. The amount of phase advance, indicated as $N^0$, required to minimize the magnitude of DC error signal 1513 is thus proportional to oxygen concentration. The value of $N^0$ is output via digital output line 1519 for further processing and interpretation, either by embedded processes or by a host computer.

Figure 16:
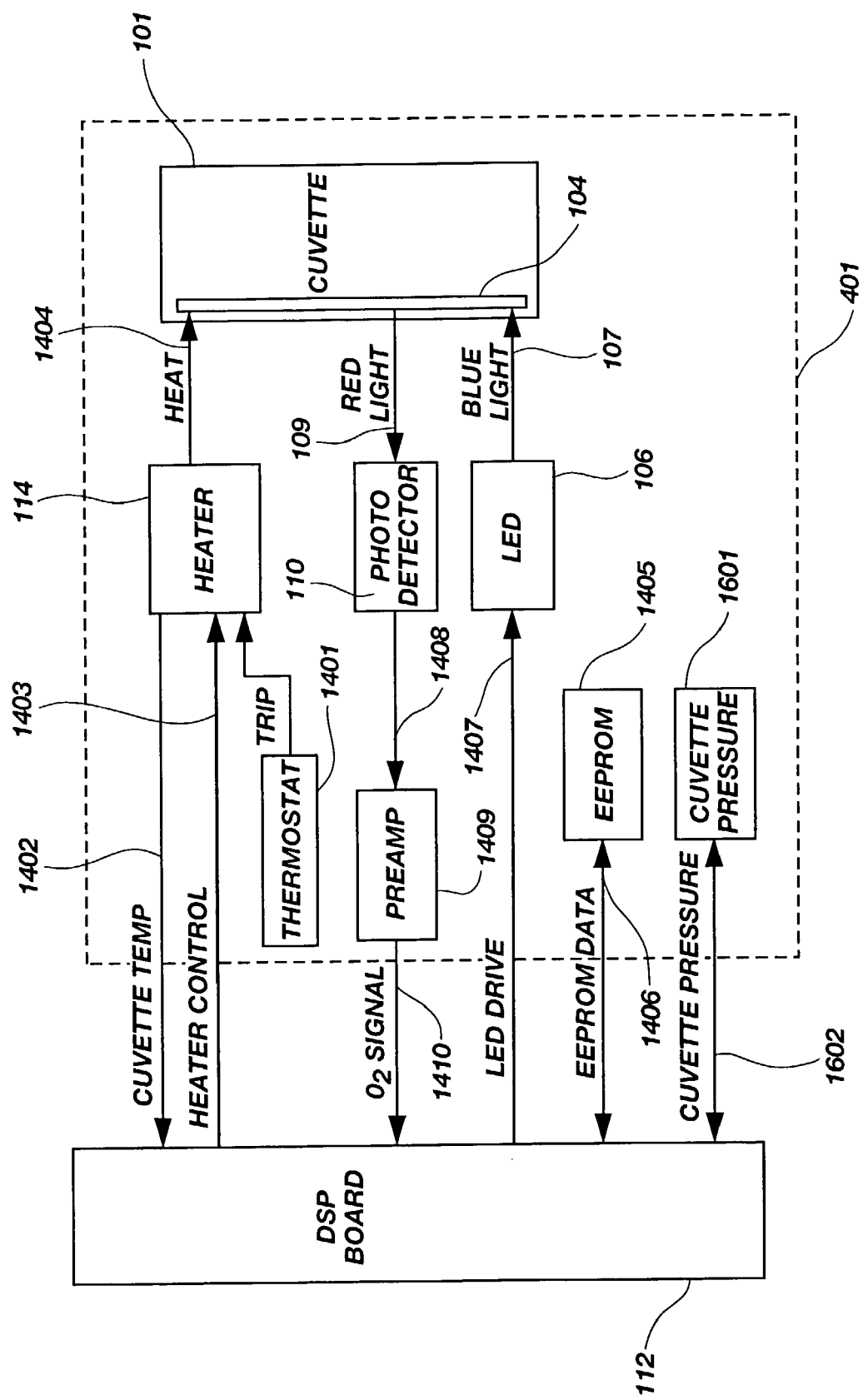
FIG. 16 is a block diagram of a DSP-based controller adapted for a sidestream embodiment of the invention, showing especially functionality of the transducer-cuvette assembly.

FIG. 16 is a block diagram of controller components for a sidestream gas measurement transducer and cuvette such as the system shown in FIGS. 10, 12, and 13 focusing especially on functionality incorporated in transducer/cuvette assembly 401. FIG. 16 also corresponds relatively closely to FIG. 14, which is an implementation specific to a mainstream gas measurement system.

The main difference between the block diagram of FIG. 16 and the block diagram of FIG. 14, aside from the physical implementation, is the addition of a pressure-sensing transducer 1601 and corresponding data line 1602 in the block diagram of FIG. 16. Because gases delivered to sidestream gas analysis systems are pumped to the sampling cuvette 101, there is a possibility of an overpressure situation in which the gas pressure within cuvette 101 is above atmospheric pressure. As was described in conjunction with FIG. 2, a higher sample gas pressure could lead to mistaken calculation of a higher-than-actual oxygen concentration.

The addition of pressure-sensing transducer 1601 yields two advantages. First, oxygen concentration calculated using an atmospheric pressure assumption may be corrected according to measured pressure to yield actual oxygen concentration. Secondly, feedback control may be used to control the pump (not shown) to reduce actual sample volume pressure to atmospheric pressure.

Other functionality of the block diagram of FIG. 16 is similar to corresponding features shown and described in FIG. 14.

Figure 17:
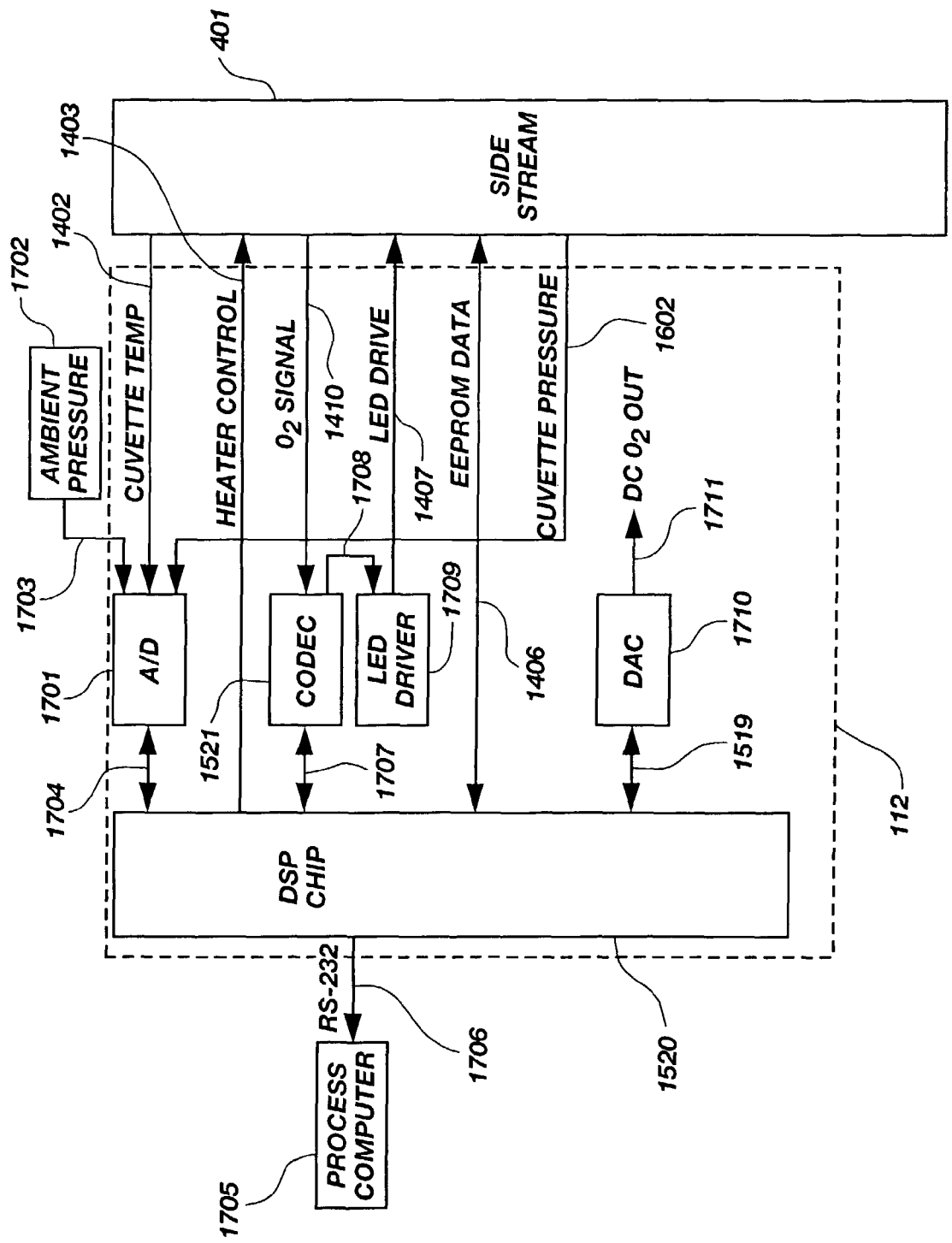
FIG. 17 is a block diagram of a controller for a sidestream gas measurement system, showing especially functionality of the DSP controller, with correction for pressure and various output interfaces.

FIG. 17 is a block diagram of a sidestream gas measurement controller showing especially functionality incorporated in the DSP controller 112. Signals from transducer/cuvette assembly 401 are as shown and described in FIG. 16.

Analog-to-digital (AID) converter 1701 is configured as a multichannel device, receiving analog input from various sensors and providing digital representations of said analog signals to the integrated circuit 1520 via digital signal path or line 1704. Cuvette temperature signal 1402 is provided as a DC voltage and converted by A/D converter 1701 into a digital form for processing by DSP chip 1520 which, in response, modulates PWM heater control line 1403. An ambient pressure transducer 1702 is connected to A/D converter 1701 by analog line 1703 and the cuvette pressure-sensing transducer 1601 (not shown) is connected to A/D converter 1701 by analog data line 1602. These analog signals are converted to corresponding digital signals and transmitted to DSP chip 1520 via digital line 1704. Digital line 1704 may, for instance, be configured as a multichannel parallel interface. By comparing the ambient pressure to cuvette pressure differential, DSP chip 1520 may, for instance, provide feedback to process computer 1705 to enable pump control. By measuring cuvette pressure, DSP chip 1520 may correct for errors in measured oxygen concentration due to absolute pressure variations.

DSP controller 112 may communicate with process computer 1705 via a serial data communications line or interface 1706. Serial communications interface 1706 may use, for instance, an RS-232 protocol. Communications interface 1706 may utilize fixed commands by the process computer 1705 to control and calibrate DSP controller 112. In one embodiment, oxygen concentration data is sent from DSP controller 112 to process computer 1705 as a response to command by the process computer. In this way, the process computer only receives data when such data is needed and it is ready to receive data.

CODEC 1521 receives an oxygen signal 1410 from the sidestream assembly 401, converts it into digital signal 1508, and transmits digital signal 1508 to DSP chip 1520 as shown and described in FIG. 15. CODEC 1521 provides an interface between the digital input and output (I/O) of DSP chip 1520 and various analog lines, only two of which are shown in FIG. 17 for clarity. Digital interface 1707 is actually a composite of several digital channels including 1508, 1509, 1515, and 1516. CODEC 1521 converts a digital LED drive signal or wave form transmitted along channel 1515 into a corresponding LED analog signal 1708. LED analog signal 1708 is then amplified by LED driver 1709 and sent to sidestream assembly 401 via LED drive 1407 to drive LED 106 (not shown).

EEPROM data line 1406 operates as shown and described in FIGS. 14 and 16.

Digital output line 1519 is converted to an analog signal or line 1711 by digital-to-analog converter (DAC) (elsewhere referred to as "D/A converter") 1710. Analog line 1711 may be used, for instance, to drive analog gauges or other devices for displaying oxygen concentration data to a user.

While the invention is described and illustrated here in the context of a limited number of preferred embodiments, the invention may be embodied in many forms without departing from the spirit of the essential characteristics of the invention. The present embodiments are, therefore, to be considered in all respects as illustrative and not restrictive. The scope of the invention is indicated by the appended claims rather than by the forgoing description, and all changes which come within the meaning and range of equivalency of the claims are intended to be embraced therein.

What is claimed is:

1. A sampling device of a respiratory gas sensor comprising:
   a housing including an interconnection component configured to be received by a complementary interconnection component of a transducer for temporary assembly of the sampling device with the transducer;
   a flow passage for receiving a sample, the flow passage being defined by and substantially confined within the housing;
   a luminescable material positioned within the flow passage and visible from an exterior of the housing so as to receive radiation from a source of the transducer and emit radiation for sensing by a detector of the transducer upon assembly of the transducer with the sampling device; and
   a temperature communication element operatively coupled to the housing and associated with the luminescable material so as to control a temperature of the luminescable material.

2. The sampling device of claim 1, further comprising:
   a window formed through the housing, the luminescable material exposed to the exterior of the housing through the window.

3. The sampling device of claim 2, wherein the window comprises a support supporting the luminescable material.

4. The sampling device of claim 3, wherein the luminescable material is carried by a matrix, which is carried upon the window.

5. The sampling device of claim 4, wherein the matrix is porous.

6. The sampling device of claim 5, wherein the matrix comprises a membrane.

7. The sampling device of claim 4, further comprising:
   a retention element adjacent the window and configured to receive at least an edge portion of the matrix.

8. The sampling device of claim 7, wherein the retention element comprises:
   an aperture formed in the housing and configured to receive the window; and
   the window.

9. The sampling device of claim 8, wherein the aperture receives at least an edge portion of the matrix and the window secures at least the edge portion within the aperture upon positioning of the window in the aperture.

10. The sampling device of claim 1, wherein the luminescable material is capable of emitting at least one wavelength of electromagnetic radiation that, upon exposure of the luminescable material to at least one analyzed substance, is quenched at a rate related to a quantity of the at least one analyzed substance.

11. The sampling device of claim 10, wherein the at least one analyzed substance comprises oxygen.

12. The sampling device of claim 10, wherein the quantity comprises at least one of a concentration of the at least one analyzed substance and a partial pressure of the at least one analyzed substance in a mixture comprising at least one gaseous component.

13. The sampling device of claim 1, wherein the temperature communication element comprises an annular member.

14. The sampling device of claim 1, wherein the temperature communication element is configured to maintain at least the luminescable material at a substantially constant temperature.

15. The sampling device of claim 1, wherein the temperature communication element is configured to prevent moisture from collecting on a contacted structure.

16. The sampling device of claim 1, wherein the temperature communication element is configured to be coupled with a temperature control element of a transducer with which the housing is configured to be coupled.

17. The sampling device of claim 1, wherein the temperature communication element comprises a temperature control element.

18. The sampling device of claim 1, wherein the housing is configured to be positioned along a length of a breathing circuit.

19. The sampling device of claim 1, wherein the housing comprises a housing of a sidestream sampling cell.

20. A respiratory gas sensor, comprising:
   a sampling device, comprising:
      a housing;
      a flow passage for receiving a sample, the flow passage being defined by and substantially confined within the housing;
      a luminescable material disposed within the flow passage and visible from an exterior of the housing, luminescence of the luminescable material being quenchable upon exposure thereof to at least one analyzable substance; and
      a temperature communication element in thermal communication with the luminescable material; and
   a transducer configured for assembly with at least a portion of the sampling device, the transducer comprising:
      a housing;
      a source of at least one wavelength of electromagnetic radiation within the housing, the source oriented to direct radiation toward the luminescable material upon assembly of the transducer with the sampling device; and
      a detector within the housing, the detector being oriented to sense radiation from the luminescable material upon assembly of the transducer with the sampling device.

21. The respiratory gas sensor of claim 20, further comprising a window defined in the housing.

22. The respiratory gas sensor of claim 21, wherein the window carries at least one of the luminescable material and a matrix by which the luminescable material is carried.

23. The respiratory gas sensor of claim 22, wherein the temperature communication element contacts at least one of the window and the matrix.

24. The respiratory gas sensor of claim 20, wherein the luminescable material is capable of emitting at least one wavelength of electromagnetic radiation that, upon exposure of the luminescable material to the at least one analyzed substance, is quenched at a rate related to a quantity of the at least one analyzed substance in the sample.

25. The respiratory gas sensor of claim 24, wherein the at least one analyzed substance comprises oxygen.

26. The respiratory gas sensor of claim 20, wherein the temperature communication element is configured to maintain at least the luminescable material at a substantially constant temperature.

27. The respiratory gas sensor of claim 20, wherein the temperature communication element comprises a temperature control element.

28. The respiratory gas sensor of claim 20, wherein the temperature communication element is configured to be operatively coupled with a temperature control element.

29. The respiratory gas sensor of claim 20, wherein the transducer further comprises:
   a temperature control element that communicates with the temperature communication element upon placement of the sampling device and the transducer in the assembled relationship.

30. The respiratory gas sensor of claim 20, wherein at least one of the sampling device and the transducer comprises an interconnection element.

31. The respiratory gas sensor of claim 30, wherein the interconnection element is configured to prevent misalignment between the sampling device and the transducer.

32. The respiratory gas sensor of claim 20, wherein the sampling device is configured to be positioned along a length of a breathing circuit.

33. The respiratory gas sensor of claim 20, wherein the housing of the sampling device comprises a housing of a sidestream sampling cell.

* * * * *